United States Patent
Amann et al.

(10) Patent No.: US 6,242,245 B1
(45) Date of Patent: Jun. 5, 2001

(54) MULTICOMPONENT SYSTEM FOR MODIFYING, DEGRADING OR BLEACHING LIGNIN OR LIGNIN-CONTAINING MATERIALS, AND PROCESSES FOR ITS USE

(75) Inventors: Manfred Amann, Odelhausen; Michael Wohlschlager, Eichenau; Johannes Freudenreich, Munich; Jürgen Stohrer, Pullach; Elke Fritz-Langhals, Ottobrunn, all of (DE)

(73) Assignee: Consortium für elektrochemische Industrie GmbH, Munich (DE)

( * ) Notice: Subject to any disclaimer, the term of this patent is extended or adjusted under 35 U.S.C. 154(b) by 0 days.

(21) Appl. No.: 09/160,961

(22) Filed: Sep. 25, 1998

(30) Foreign Application Priority Data

Sep. 26, 1997 (DE) ............................... 197 42 671
Feb. 5, 1998 (DE) ............................... 198 04 583

(51) Int. Cl.$^7$ ....................................... C12S 3/08
(52) U.S. Cl. ..................... 435/277; 435/278; 162/72; 510/305; 510/306; 510/320
(58) Field of Search ................... 435/277, 278, 435/267; 162/70–72; 510/305, 306, 320, 321

(56) References Cited

U.S. PATENT DOCUMENTS 5,374,555    12/1994   Pokora et al. .
5,866,392 *  2/1999    Schou et al. .

FOREIGN PATENT DOCUMENTS

| 0487557 | 2/1996 | (EP) . |
|---------|--------|--------|
| 9111552 | 8/1991 | (WO) . |
| 9111553 | 8/1991 | (WO) . |
| 9401538 | 1/1994 | (WO) . |
| 9429510 | 12/1994 | (WO) . |
| 9612846 | 5/1996 | (WO) . |
| 9706244 | 2/1997 | (WO) . |

OTHER PUBLICATIONS

Oxidative Bleaching Enzymes: A Review, Paice, M.G., et al., 1995.
Role of Xylanase in Laccase–Mediator del. of Kraft Pulps, Ohsanen et al., 1997.
Enzyme Nomenclature, Academic Press, Inc., 1992, pp. 21–154.
Amann, 1997, "The Lignozym Process–Coming Closer to the Mill".

* cited by examiner

Primary Examiner—William H. Beisner
(74) Attorney, Agent, or Firm—Collard & Roe, P.C.

(57) ABSTRACT

A multicomponent system for modifying, degrading or bleaching lignin and lignin-containing materials or similar substances, includes an oxidoreductase and an oxidant suitable for the oxidoreductase and a mediator and at least one enzymatically active additive. The mediator does not inactivate the oxidoreductase and the enzymatically active additive, and the enzymatically active additive is selected from the group consisting of the hydrolases of the enzyme class 3.2.1.

10 Claims, No Drawings

US 6,242,245 B1

MULTICOMPONENT SYSTEM FOR MODIFYING, DEGRADING OR BLEACHING LIGNIN OR LIGNIN-CONTAINING MATERIALS, AND PROCESSES FOR ITS USE

BACKGROUND OF THE INVENTION

1. Field of the Invention

The present invention relates to a multicomponent system for modifying, degrading or bleaching lignin or lignin-containing materials, and processes for its use.

2. The Prior Art

The primary objective of all processes for the preparation of pulp is the removal of the lignin from the plant starting material. This objective is achieved by using suitable oxidative or reductive chemical process steps which ultimately modify the lignin in a manner in which it can easily be extracted from the pulp product. Traditionally, chlorine or chlorine-containing chemicals, such as hypochlorite or chlorine dioxide, are used in the chemical process steps.

Recently, instead of or in addition to these chlorine-containing compounds, chlorine-free chemicals have been employed. These include, for example, oxygen, hydrogen peroxide, peroxyacids or ozone. Typically, the pulp to be processed is subjected to an extraction step which contains alkali, e.g. NaOH, between the various chemical treatments.

As an additional chlorine-free process step in the chemical processes for the removal of lignin, enzymatic processes are known which should facilitate the chemical removal of the lignin in a multistage delignifier and bleaching sequence. This process step can be carried out as one or more stages in sequential combination with chemical process steps (WO 91/11553). Advantages of this process step include an improvement in the degrees of whiteness which can be achieved. There is also a reduction in the chemical requirement, especially in the amount of chlorine employed.

Using EP 0 487 557 discloses additionally individual enzymes or mixtures of enzymes of related classes in chemical delignification processes using oxygen. These are, for example, enzyme preparations which contain various hemicellulases.

U.S. Pat. No. 5,374,555 discloses a chemical process with additional enzymatic pulp treatment using enzymes from the proteases group. This treatment is carried out as a separate process step which leads to advantages in sequential combination with chemical process steps.

WO 91/11552 describes the use of oxidizing and hydrolytic enzymes in a process for the mechanical production of mechanical pulp. Additives such as ascorbic acid are used to adjust the redox potential to values of <200 mV.

In addition to the use of enzymatic processes combined with chemical processes for the treatment of the pulp, enzymatic processes only used for the treatment of the pulp are also described.

Such processes utilize phenol-oxidizing enzymes. Examples of such enzymes are those from the peroxidases (E.C.1.11.1) and oxidases group (E.C.1.10.3). The enzymes either use hydrogen peroxide or molecular oxygen as an electron acceptor. The use of these oxidative enzymes in bleaching is described (e.g. Paice, M. G., 1995). Manganese peroxidase (MnP), lignin peroxidase (LiP) or laccase (E.C.1.10.3.2), for example, are used. Whereas LiP and MnP typically require hydrogen peroxide as a cosubstrate, laccase works with oxygen as an electron acceptor.

It was still not possible to use peroxidases successfully in bleaching. This is because up to now it has not been possible to solve the problem of peroxidase inactivation by hydrogen peroxide. Also there is no suitable metering technique for hydrogen peroxide in a batchwise industrial process.

The sole use of laccase does not convert the lignin into the desired extractable form. It was possible by addition of suitable mediator substances to laccase to develop an industrial process which can successfully delignify pulp of any type. Such an enzymatic delignifier system, which consists of the components laccase, mediator and oxygen, is described in WO 94/29510.

Further mediators for enzymatic delignifications using laccase are described in WO 7/06244 9.

WO 94/01538 describes the use of cellobiose oxidase in combination with an endoglycanase, for example xylanase and/or oxidoreductase, for example laccase. Moreover, a bleach enhancer is also added in the process. The conditions indicated include an alkaline pH. The efficiency of such a system is very low, since at the pH mentioned the laccase described is largely inactive. Moreover, laccase is inactivated in the presence of hydrogen peroxide. There is also the fact that the compounds mentioned as bleach enhancers show no enhancer activity. This is evident from WO 96/12846, where a use analogous to pulp bleaching, the bleaching of dyed textile fibers, is described:

In Example 1, WO 96/12846 describes the efficiency of different mediators. As is evident from Table 2 in this example, the exemplary compounds mentioned there show no mediator activity.

WO 94/29510 describes the advantageous combination of an enzymatic delignifier system consisting of a laccase and an active mediator. This process is the only known enzymatic process at present which leads to an effective breakdown of lignin. The mediator used here is N—OH-benzotriazole (HBT). In the process described, the addition of further enzymatic components, such as, proteases, is also mentioned.

As shown by oksanen et al. 1997, a combined use of xylanase/laccase/HBT shows only a very slight improvement compared with a xylanase-free use. Advantages resulted only after the xylanase treatment was separated from the laccase/HBT treatment and was carried out as a unique process step.

It is therefore desirable to have available a multicomponent system for modifying, degrading or bleaching lignin and lignin-containing materials. This system achieves better results in delignification than known enzymatic delignification systems and is not affected by the disadvantages of chemical delignification systems.

In addition to the poor performance of the individual enzymatic processes for pulp delignification, the isolation of enzymatic delignification stages on account of the problems described above and the stepwise procedure in the delignification of pulp resulting therefrom is a considerable disadvantage of these processes. Due to the necessity of washing and extraction steps between the different enzyme treatments, the processes cannot be integrated economically into the existing delignification and bleaching sequences.

It is therefore also desirable to have available enzymatic processes for the treatment of lignin and lignin-containing materials which combine several enzymatic process steps in a single process stage.

SUMMARY OF THE INVENTION

The present invention relates to a multicomponent system or composition for modifying, degrading or bleaching lignin, lignin-containing materials or similar substances, comprising an oxidoreductase, an oxidant suitable for the oxidoreductase, a mediator and at least one enzymatically active additive, wherein the mediator does not inactivate the oxidoreductase and the enzymatically active additive, and the enzymatically active additive is selected from the hydrolases group of the enzyme class 3.2.1.

The naming of the enzyme classes is carried out in the present application according to International Enzyme Nomenclature, Committee of the International Union of Biochemistry and Molecular Biology (Enzyme Nomenclature, Academic Press, Inc., 1992, pp. 24–154).

Within the meaning of the invention, a mediator inactivates an enzyme if it brings about a loss of >70% of the enzyme activity of this enzyme within an incubation time of 30 min. This takes place in a test system which contains, in a total volume of 50 ml at 45° C., 60 IU of oxidoreductase, for example laccase and 400 IU of hydrolase of the enzyme class 3.2.1, for example xylanase, cellulase or a corresponding amount of another enzyme, and also 7.5 mmol/l of mediator.

The multicomponent system or composition according to the invention has the following advantages compared with the prior art:

It has a high selectivity for lignin

It does not adversely affect the fiber quality

In combination with chemical delignification processes, it makes possible a saving of chemicals in the overall delignification and bleaching It represents an improvement in the previous individual processes of xylanase treatment and laccase mediator system. The improvement is greater than the sum of the individual processes.

The use of cellulase in processes for the production of pulp was previously unknown. Since cellulases, as is known, degrade cellulose and thus, according to present opinion, always damage pulp, their use in the process for the production of pulp is completely unexpected and surprising to the person skilled in the art.

Oxidoreductases which can be employed in the multicomponent system according to the invention are oxidoreductases of classes 1.1.1 to 1.97 according to International Enzyme Nomenclature, Committee of the International Union of Biochemistry and Molecular Biology (Enzyme Nomenclature, Academic Press, Inc., 1992, pp. 24–154).

Preferably, oxidoreductases of the classes mentioned in the following are employed:

Enzymes of class 1.1, which include all dehydrogenases which act on primary or secondary alcohols and semiacetals, and which as acceptors have $NAD^+$ or $NADP^+$ (subclass 1.1.1), cytochrome (1.1.2), oxygen ($O_2$) (1.1.3), disulfides (1.1.4), quinones (1.1.5) or other acceptors (1.1.99).

Particularly preferred from this class are the enzymes of class 1.1.5 with quinones as acceptors and the enzymes of class 1.1.3 with oxygen as the acceptor.

Particularly preferred in this class is cellobiose: quinone-1-oxidoreductase (1.1.5.1).

Additionally preferred are enzymes of class 1.2. This enzyme class includes those enzymes which oxidize aldehydes to the corresponding acids or oxo groups. The acceptors can be $NAD^+$, $NADP^+$ (1.2.1), cytochrome (1.2.2), oxygen (1.2.3), sulfides (1.2.4), iron-sulfur proteins (1.2.5) or other acceptors (1.2.99).

Particularly preferred here are the enzymes of the group (1.2.3) with oxygen as an acceptor.

Additionally preferred are enzymes of class 1.3. Enzymes in this class are those which act on CH—CH groups of the donor.

The corresponding acceptors are $NAD^+$, $NADP^+$ (1.3.1), cytochromes (1.3.2), oxygen (1.3.3), quinones or related compounds (1.3.5), iron-sulfur proteins (1.3.7) or other acceptors (1.3.99). Particularly preferred is bilirubin oxidase (1.3.3.5).

Here, the enzymes of the class (1.3.3) with oxygen as an acceptor and (1.3.5) with quinones etc. as an acceptor are likewise particularly preferred.

Additionally preferred are enzymes of the class 1.4, which act on CH—$NH_2$ groups of the donor. The corresponding acceptors are $NAD^+$, $NADP^+$ (1.4.1), cytochromes (1.4.2), oxygen (1.4.3), disulfides (1.4.4), iron-sulfur proteins (1.4.7) or other acceptors (1.4.99). Also particularly preferred here are enzymes of the class 1.4.3 with oxygen as an acceptor.

Additionally preferred are enzymes of the class 1.5, which act on CH—NH groups of the donor. The corresponding acceptors are $NAD^+$, $NADP^+$ (1.5.1), oxygen (1.5.3), disulfides (1.5.4), quinones (1.5.5) or other acceptors (1.5.99). Also particularly preferred here are enzymes with oxygen ($O_2$) (1.5.3) and with quinones (1.5.5) as acceptors.

Additionally preferred are enzymes of the class 1.6, which act on NADH or NADPH. The acceptors here are $NADP^+$ (1.6.1), hemeproteins (1.6.2), disulfides (1.6.4), quinones (1.6.5), $NO_2$ groups (1.6.6) and a flavin (1.6.8) or some other acceptors (1.6.99).

Particularly preferred here are enzymes of the class 1.6.5 with quinones as acceptors.

Additionally preferred are enzymes of the class 1.7, which act on other $NO_2$ compounds as donors and as acceptors have cytochromes (1.7.2), oxygen ($O_2$) (1.7.3), iron-sulfur proteins (1.7.7) or others (1.7.99). Particularly preferred here is the class 1.7.3 with oxygen as an acceptor.

Additionally preferred are enzymes of the class 1.8, which act on sulfur groups as donors and as acceptors have $NAD^+$, $NADP^+$ (1.8.1), cytochrome (1.8.2), oxygen ($O_2$) (1.8.3), disulfides (1.8.4), quinones (1.8.5), iron-sulfur proteins (1.8.7) or others (1.8.99). Particularly preferred is the class 1.8.3 with oxygen ($O_2$) and (1.8.5) with quinones as acceptors.

Additionally preferred are enzymes of the class 1.9, which act on heme groups as donors and as acceptors have oxygen ($O_2$) (1.9.3), $NO_2$ compounds (1.9.6) and others (1.9.99). Particularly preferred here is the group 1.9.3 with oxygen ($O_2$) as an acceptor (cytochrome oxidases).

Additionally preferred are enzymes of the class 1.12, which act on hydrogen as donor. The acceptors are $NAD^+$ or $NADP^+$ (1.12.1) or others (1.12.99). Additionally preferred are enzymes of the class 1.13 and 1.14 (oxygenases).

Furthermore preferred are enzymes of the class 1.15, which act on superoxide radicals as acceptors. Particularly preferred here is superoxide dismutase (1.15.1.1).

Furthermore preferred are enzymes of the class 1.16. $NAD^+$ or $NADP^+$ (1.16.1) or oxygen ($O_2$) (1.16.3) act as acceptors. Particularly preferred here are enzymes of the class 1.16.3.1 (ferroxidase, e.g. ceruloplasmin).

Enzymes furthermore preferred are those which belong to the group 1.17 (action on $CH_2$ groups, which are oxidized to —CHOH—), 1.18 (action on reduced ferredoxin as a donor), 1.19 (action on reduced flavodoxin as a donor) and 1.97 (other oxidoreductases).

Furthermore particularly preferred are the enzymes of the group 1.11, which act on a peroxide as an acceptor. This individual subclass (1.11.1) contains the peroxidases.

Particularly preferred here are the cytochrome C peroxidases (1.11.1.5), catalase (1.11.1.6), peroxidase (1.11.1.6), iodide peroxidase (1.11.1.8), glutathione peroxidase (1.11.1.9), chloride peroxidase (1.11.1.10), L-ascorbate peroxidase (1.11.1.11), phospholipid hydroperoxide glutathione peroxidase (1.11.1.12), manganese peroxidase (1.11.1.13), diarylpropane peroxidase (ligninase, lignin peroxidase) (1.11.1.14).

Very particularly preferred are enzymes of the class 1.10, which act on biphenols and related compounds. They catalyze the oxidation of biphenols and ascorbates. NAD$^+$, NADP$^+$ (1.10.1), cytochromes (1.10.2), oxygen (1.10.3) or others (1.10.99) function as acceptors.

Of these, enzymes of the class 1.10.3 with oxygen (O$_2$) as an acceptor are in turn particularly preferred. Of the enzymes of this class, the enzymes catechol oxidase (tyrosinase) (1.10.3.1), L-ascorbate oxidase (1.10.3.3), o-aminophenol oxidase (1.10.3.4) and laccase (benzenediol: oxygen oxidoreductase) (1.10.3.2) are preferred, the laccases (benzenediol: oxygen oxidoreductase) (1.10.3.2) being particularly preferred.

The mentioned oxidoreductases are commercially available or can be obtained by standard processes. Suitable organisms for the production of the enzymes are, for example, plants, animal cells, bacteria and fungi. In principle, both naturally occurring and genetically modified organisms can be enzyme producers. Likewise, parts of monocellular or multicellular organisms are conceivable as enzyme producers, especially cell cultures.

For the particularly preferred oxidoreductases, such as those from the group 1.11.1, but especially 1.10.3, and in particular for the production of laccases, white rot fungi, for example, such as Pleurotus, Phlebia and Trametes, are used.

The multicomponent system or composition according to the invention comprises at least one oxidant. Oxidants which can be employed are, for example, air, oxygen, ozone, H$_2$O$_2$, organic peroxides, peracids such as peracetic acid, performic acid, persulfuric acid, pernitric acid, metachloroperoxybenzoic acid, perchloric acid, perborates, peracetates, persulfates, peroxides or oxygen species and their radicals such as OH, OOH, singlet oxygen, superoxide (O$_2^-$), ozonide, dioxygenyl cation (O$_2^+$), dioxiranes, dioxetanes or Fremy radicals.

Preferably, those oxidants are employed which can either be generated by the appropriate oxidoreductases, e.g. dioxiranes from laccases plus carbonyls, or which chemically regenerate the mediator or can directly convert this.

For example, peroxidases require hydrogen peroxide as a cosubstrate. This compound can either be added directly to the system or liberated from a precursor compound. Finally, hydrogen peroxide can also be formed in situ by an auxiliary reaction, e.g. by the enzymatic reaction of glucose with glucose oxidase (E.C. 1.1.3.4).

For example, oxidases use oxygen as an electron acceptor. Oxygen is customarily dissolved in an adequate amount in aqueous solutions. However, oxygen can also be introduced into the reaction solution by suitable measures, such as stirring, use of oxygen gas or the application of pressure. This is particularly necessary if the process is to be operated at elevated temperature, since the solubility of oxygen in aqueous solutions decreases with increasing temperature.

The multicomponent system according to the invention comprises at least one mediator which does not inactivate the oxidoreductase and the enzymatically active additive.

The mediator selected is preferably at least one compound from the group consisting of the aliphatic, cycloaliphatic, heterocyclic or aromatic compounds, which contains at least one N-hydroxy, oxime, nitroso, N-oxyl or N-oxy function, where substituted or unsubstituted 1-hydroxy-1- benzotriazoles, 3H-benzotriazole-1-oxides and 2H-benzotriazole-1-oxides are excluded.

Examples of such compounds are the compounds of the formula I, II or III mentioned below, the compounds of the formulae II and III being preferred.

Compounds of the general formula I are:

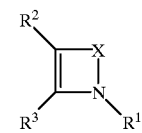

where X is one of the following groups:

(—N=CR$^4$—)$_p$, (—CR$^4$=N—)$_p$, (—CR$^5$=CR$^6$)$_p$ and p is equal to 1 or 2, where the radicals R$^1$ to R$^6$ can be identical or different and independently of one another can be one of the following groups: hydrogen, halogen, hydroxyl, formyl, carboxyl and salts and esters thereof, amino, nitro, C$_1$–C$_{12}$-alkyl, C$_1$–C$_6$-alkyloxy, carbonyl-C$_1$–C$_6$-alkyl, phenyl, sulfono, esters and salts thereof, sulfamoyl, carbamoyl, phospho, phosphono, phosphonooxy and their salts and esters, where the amino, carbamoyl and sulfamoyl groups of the radicals R$^1$ to R$^6$ can furthermore be unsubstituted or mono- or disubstituted by hydroxyl, C$_1$–C$_3$-alkyl or C$_1$–C$_3$-alkoxy, and where the radicals R$^2$ and R$^3$ form a common group —A— and —A— in this case represents one of the following groups: (—CR$^7$=CR$^8$—CR$^9$=CR$^{10}$—) or (—CR$^{10}$=CR$^9$—CR$^8$=CR$^7$—).

The radicals R$^7$ to R$^{10}$ can be identical or different and independently of one another are one of the following groups: hydrogen, halogen, hydroxyl, formyl, carboxyl and salts and esters thereof, amino, nitro, C$_1$–C$_{12}$-alkyl, C$_1$–C$_6$-alkyloxy, carbonyl-C$_1$–C$_6$-alkyl, phenyl, sulfono, esters and salts thereof, sulfamoyl, carbamoyl, phospho, phosphono, phosphonooxy and their salts and esters, where the amino, carbamoyl and sulfamoyl groups of the radicals R$^7$ to R$^{10}$ can furthermore be unsubstituted or mono- or disubstituted by hydroxyl, C$_1$–C$_3$-alkyl, C$_1$–C$_3$-alkoxy and where the C$_1$–C$_{12}$-alkyl, C$_1$–C$_6$-alkyloxy, carbonyl-C$_1$–C$_6$-alkyl, phenyl and aryl groups of the radicals R$^7$ to R$^{10}$ can be unsubstituted or furthermore mono- or disubstituted by the radical R$^{11}$ and where the radical R$^{11}$ can be one of the following groups: hydrogen, halogen, hydroxyl, formyl, carboxyl and their salts and esters, amino, nitro, C$_1$–C$_{12}$-alkyl, C$_1$–C$_6$-alkyloxy, carbonyl-C$_1$–C$_6$-alkyl, phenyl, aryl, and their esters and salts, where the carbamoyl, sulfamoyl and amino groups of the radical R$^{11}$ can be unsubstituted or furthermore mono- or disubstituted by the radical R$^{12}$ and where the radical R$^{12}$ can be one of the following groups: hydrogen, hydroxyl, formyl, carboxyl and their salts and esters, amino, nitro, C$_1$–C$_{12}$-alkyl, C$_1$–C$_6$-alkyloxy, carbonyl-C$_1$–C$_6$-alkyl, phenyl or aryl.

Compounds of the general formula II are:

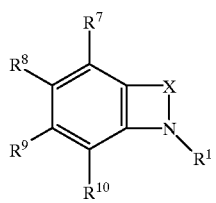

formula II are:
where X is one of the following groups:
($-$N$=$CR$^4-$)$_p$, ($-$CR$^4=$N$-$)$_p$, ($-$CR$^5=$CR$^6$)$_p$ and p is equal to 1 or 2.

The radicals $R^1$ and $R^4$ to $R^{10}$ can be identical or different and independently of one another are one of the following groups: hydrogen, halogen, hydroxyl, formyl, carboxyl and salts and esters thereof, amino, nitro, $C_1$–$C_{12}$-alkyl, $C_1$–$C_6$-alkyloxy, carbonyl-$C_1$–$C_6$-alkyl, phenyl, aryl, sulfono, esters and salts thereof, sulfamoyl, carbamoyl, phospho, phosphono, phosphonooxy and their salts and esters, where the amino, carbamoyl and sulfamoyl groups of the radicals $R^1$ and $R^4$ to $R^{10}$ can furthermore be unsubstituted or mono- or disubstituted by hydroxyl, $C_1$–$C_3$-alkyl or $C_1$–$C_3$-alkoxy, and where the $C_1$–$C_{12}$-alkyl, $C_1$–$C_6$-alkyloxy, carbonyl-$C_1$–$C_6$-alkyl, phenyl, aryl and aryl-$C_1$–$C_6$-alkyl groups of the radicals $R^1$ and $R^4$ to $R^{10}$ can be unsubstituted or furthermore mono- or polysubstituted by the radical $R^{12}$ and where the radical $R^{12}$ can be one of the following groups: hydrogen, halogen, hydroxyl, formyl, carboxyl and their salts and esters, amino, nitro, $C_1$–$C_{12}$-alkyl, $C_1$–$C_6$-alkyloxy, carbonyl-$C_1$–$C_6$-alkyl, phenyl, aryl, sulfono, sulfeno, sulfino and their esters and salts, and where the carbamoyl, sulfamoyl and amino groups of the radical $R^{12}$ can be unsubstituted or furthermore mono- or disubstituted by the radical $R^{13}$ and where the radical $R^{13}$ can be one of the following groups: hydrogen, hydroxyl, formyl, carboxyl and their salts and esters, amino, nitro, $C_1$–$C_{12}$-alkyl, $C_1$–$C_6$-alkyloxy, carbonyl-$C_1$–$C_6$-alkyl, phenyl or aryl.

Examples of the compounds mentioned are:
1-Hydroxybenzimidazoles
1-hydroxybenzimidazole-2-carboxylic acid
1-hydroxybenzimidazole
2-methyl-1-hydroxybenzimidazole
2-phenyl-1-hydroxybenzimidazole
1-Hydroxyindoles
2-phenyl-1-hydroxyindole Substances of the general formula III are:

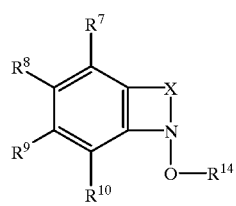

where X is one of the following groups:
($-$N$=$CR$^4-$)$_m$, ($-$CR$^4=$N$-$)$_m$, ($-$CR$^5=$CR$^6-$)$_m$ and m is equal to 1 or 2.

What has been said above applies to the radicals $R^7$ to $R^{10}$ and $R^4$ to $R^6$.

$R^{14}$ can be: hydrogen, $C_1$–$C_{10}$-alkyl, $C_1$–$C_{10}$-alkylcarbonyl, of which $C_1$–$C_{10}$-alkyl and $C_1$–$C_{10}$-alkylcarbonyl can be unsubstituted or mono- or polysubstituted by a radical $R^{15}$, where $R^{15}$ can be one of the following groups:
hydrogen, halogen, hydroxyl, formyl, carboxyl and salts and esters thereof, amino, nitro, $C_1$–$C_{12}$-alkyl, $C_1$–$C_6$-alkyloxy, carbonyl-$C_1$–$C_6$-alkyl, phenyl, sulfono, their esters and salts, sulfamoyl, carbamoyl, phospho, phosphono, phosphonooxy and their salts and esters, where the amino, carbamoyl and sulfamoyl groups of the radical $R^{15}$ can furthermore be unsubstituted or mono- or disubstituted by hydroxyl, $C_1$–$C_3$-alkyl or $C_1$–$C_3$-alkoxy.

The mediator can preferably also be selected from the group of cyclic N-hydroxy compounds having at least one optionally substituted five or six-membered ring, comprising the structure mentioned in formula IV

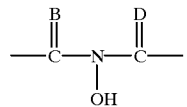

and their salts, ethers or esters, where

B and D are identical or different and are O, S or NR$^{16}$, where $R^{16}$ is a hydrogen, hydroxyl, formyl, carbamoyl or sulfono radical, ester or salt of the sulfono radical, sulfamoyl, nitro, amino, phenyl, aryl-$C_1$–$C_5$-alkyl, $C_1$–$C_{12}$-alkyl, $C_1$–$C_5$-alkoxy, $C_1$–$C_{10}$-carbonyl, carbonyl-$C_1$–$C_6$-alkyl, phospho, phosphono or phosphonooxy radical, or an ester or salt of the phosphonooxy radical, where carbamoyl, sulfamoyl, amino and phenyl radicals can be unsubstituted or mono- or polysubstituted by a radical $R^{17}$ and the aryl-$C_1$–$C_5$-alkyl, $C_1$–$C_{12}$-alkyl, $C_1$–$C_5$-alkoxy, $C_1$–$C_{10}$-carbonyl and carbonyl-$C_1$–$C_6$-alkyl radicals can be saturated or unsaturated, branched or unbranched and can be mono- or polysubstituted by a radical $R^{17}$ where $R^{17}$ is identical or different and is a hydroxyl, formyl or carboxyl radical, ester or salt of the carboxyl radical, carbamoyl or sulfono radical, ester or salt of the sulfono radical, sulfamoyl, nitro, amino, phenyl, $C_1$–$C_5$-alkyl or $C_1$–$C_5$-alkoxy radical.

The mediator is preferably selected from the group of compounds of the general formula V, VI, VII or VIII

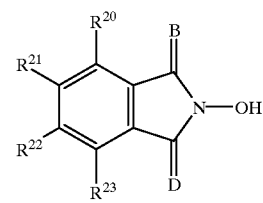

-continued

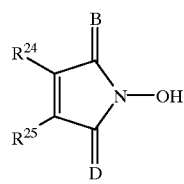
VI

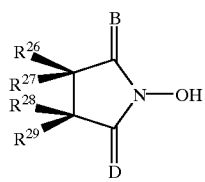
VII

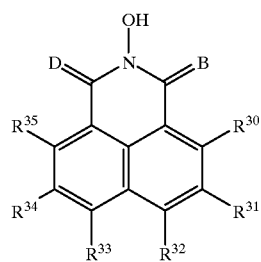
VIII where B and D have the meanings already mentioned and the radicals $R^{18}$–$R^{33}$ are identical or different and are a halogen radical, carboxyl radical, salt or ester of a carboxyl radical or have the meanings mentioned for $R^{16}$, where $R^{24}$ and $R^{25}$ or $R^{26}$ and $R^{27}$ must not simultaneously be a hydroxyl or amino radical and if appropriate two each of the substituents $R^{18}$–$R^{21}$, $R^{22}$–$R^{23}$, $R^{24}$–$R^{27}$ and $R^{28}$–$R^{33}$ can be linked to give a ring —E—, where —E— has one of the following meanings:

(—CH═CH—)$_n$ where n=1 to 3, —CH═CH—CH═N— or

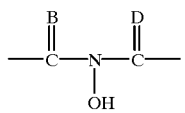
IV and where, if appropriate, the radicals $R^{24}$–$R^{27}$ can be bonded to one another by one or two bridging elements —F—, where —F— is identical or different and has one of the following meanings: —O—, —S—, —CH$_2$—, —CR$^{34}$═CR$^{35}$—;
where $R^{34}$ and $R^{35}$ are identical or different and have the meaning of $R^{18}$.

Particularly preferred as mediators are compounds of the general formulae V, VI, VII and VIII in which B and D are O or S.

Examples of compounds of this type are N-hydroxyphthalimide and optionally substituted N-hydroxyphthalimide derivatives, N-hydroxymaleimide and optionally substituted N-hydroxymaleimide derivatives, N-hydroxynaphthalimide and optionally substituted N-hydroxynaphthalimide derivatives, N-hydroxysuccinimide and optionally substituted N-hydroxysuccinimide derivatives, preferably those in which the radicals $R^{24}$–$R^{27}$ are bonded polycyclically.

Particularly preferred as mediators are N-hydroxyphthalimide, 4-amino-N-hydroxyphthalimide and 3-amino-N-hydroxyphthalimide.

Compounds of the formula V suitable as mediators are, for example:
N-hydroxyphthalimide,
4-amino-N-hydroxyphthalimide,
3-amino-N-hydroxyphthalimide,
N-hydroxybenzene-1,2,4-tricarboximide,
N,N'-dihydroxypyromellitic diimide,
N,N'-dihydroxybenzophenone-3,3',4,4'-tetracarboxylic diimide.

Compounds of the formula VI suitable as mediators are, for example:
N-hydroxymaleimide,
pyridine-2,3-dicarboxylic acid N-hydroxyimide.

Compounds of the formula VII suitable as mediators are, for example:
N-hydroxysuccinimide,
N-hydroxytartarimide,
N-hydroxy-5-norbornene-2,3-dicarboximide,
exo-N-hydroxy-7-oxabicyclo[2.2.1]-hept-5-ene-2,3-dicarboximide,
N hydroxy-cis-cyclohexane-1,2-dicarboximide,
N-hydroxy-cis-4-cyclohexene-1,2-dicarboximide.

A compound of the formula VIII suitable as a mediator is, for example:
N-hydroxynaphthalimide sodium salt.

A compound having a six-membered ring comprising the structure mentioned in formula IV suitable as a mediator is, for example:
N-hydroxyglutarimide.

The compounds mentioned by way of example are also suitable in the form of their salts or esters as mediators.

Also suitable as mediators are compounds selected from the N-aryl-N-hydroxyamides group.

Of these, preferably employed as mediators are compounds of the general formula IX, X or XI

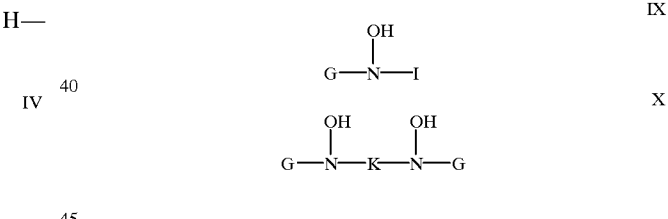

and their salts, ethers or esters, where

G is a monovalent homo- or heteroaromatic mono- or binuclear radical and

L is a divalent homo- or heteroaromatic mono- or binuclear radical and where these aromatics can be substituted by one or more, identical or different radicals $R^{36}$, selected from the group consisting of a halogen, hydroxyl, formyl, cyano, carbamoyl or carboxyl radical, ester or salt of the carboxyl radical, sulfono radical, ester or salt of the sulfono radical, sulfamoyl, nitro, nitroso, amino, phenyl, aryl-$C_1$–$C_5$-alkyl, $C_1$–$C_{12}$-alkyl, $C_1$–$C_5$-alkoxy, $C_1$–$C_{10}$-carbonyl, carbonyl-$C_1$–$C_6$-alkyl, phospho, phosphono or phosphonooxy radical, and ester or salt of the phosphonooxy radical and where carbamoyl, sulfamoyl, amino and phenyl radicals can be unsubstituted or mono- or polysubstituted by a radical $R^{37}$ and the aryl-$C_1$–$C_5$-alkyl, $C_1$–$C_{12}$-alkyl, $C_1$–$C_5$-alkoxy, $C_1$–$C_{10}$-carbonyl and carbonyl-$C_1$–$C_6$-alkyl radicals can be saturated or unsaturated, branched or unbranched and can be mono- or polysubstituted by a radical $R^{37}$, where $R^{37}$ is identical or different and is a hydroxyl, formyl, cyano or carboxyl radical, ester or salt of the carboxyl radical, carbamoyl, sulfono, sulfamoyl, nitro, nitroso, amino, phenyl, $C_1$–$C_5$-alkyl, $C_1$–$C_5$-alkoxy or $C_1$–$C_5$-alkylcarbonyl radical and each of the two radicals $R^{36}$ or $R^{37}$ can be linked in pairs via a bridge [—$CR^{38}R^{39}$—]$_m$ where m is equal to 0, 1, 2, 3 or 4 and $R^{38}$ and $R^{39}$ are identical or different and are a carboxyl radical, ester or salt of the carboxyl radical, phenyl, $C_1$–$C_5$-alkyl, $C_1$–$C_5$-alkoxy or $C_1$–$C_5$-alkylcarbonyl radical and one or more nonadjacent groups [—$CR^{38}R^{39}$—] can be replaced by oxygen, sulfur or an imino radical optionally substituted by a $C_1$ to $C_5$ alkyl radical and two adjacent groups [—$CR^{38}R^{39}$—] can be replaced by a group [—$CR^{38}$=$CR^{39}$—] and I is a monovalent acid radical present in amide form of acids selected from the group consisting of a carboxylic acid having up to 20 C atoms, carbonic acid, hemiesters of carbonic acid or carbamic acid, sulfonic acid, phosphonic acid, phosphoric acid, monoesters of phosphoric acid or diesters of phosphoric acid and K is a divalent acid radical present in amide form of acids selected from the group consisting of mono- and dicarboxylic acids having up to 20 C atoms, carbonic acid, sulfonic acid, phosphonic acid, phosphoric acid or monoesters of phosphoric acid.

Particularly preferred as mediators are compounds of the general formula XII, XIII, XIV, XV or XVI:

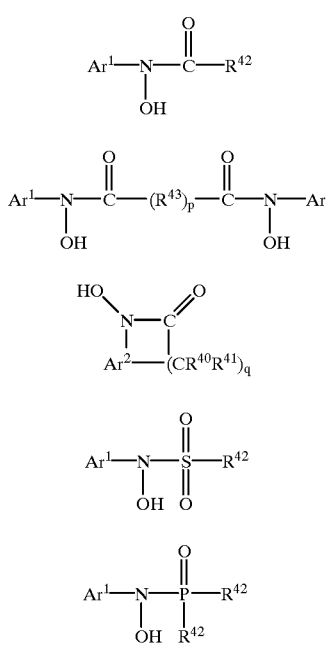

and their salts, ethers or esters, where $Ar^1$ is a monovalent homo- or heteroaromatic mononuclear aryl radical and $Ar^2$ is a divalent homo- or heteroaromatic mononuclear aryl radical, which can be substituted by one or more, identical or different radicals $R^{42}$, selected from the group consisting of a hydroxyl, cyano or carboxyl radical, ester or salt of the carboxyl radical, sulfono radical, ester or salt of the sulfono radical, nitro, nitroso, amino, $C_1$–$C_{12}$-alkyl, $C_1$–$C_5$-alkoxy, $C_1$–$C_{10}$-carbonyl and carbonyl-$C_1$–$C_6$-alkyl radical, where amino radicals can be unsubstituted or mono- or polysubstituted by a radical $R^{43}$ and the $C_1$–$C_{12}$-alkyl, $C_1$–$C_5$-alkoxy, $C_1$–$C_{10}$-carbonyl and carbonyl-$C_1$–$C_6$-alkyl radicals can be saturated or unsaturated, branched or unbranched and can be mono- or polysubstituted by a radical $R^{43}$, where $R^{43}$ is identical or different and is a hydroxyl or carboxyl radical, ester or salt of the carboxyl radical, sulfono, nitro, amino, $C_1$–$C_5$-alkyl, $C_1$–$C_5$-alkoxy or $C_1$–$C_5$-alkylcarbonyl radical and each of the two radicals $R^{42}$ can be linked in pairs via a bridge [—$CR^{38}R^{39}$—]$_m$ where m is equal to 0, 1, 2, 3 or 4 and $R^{38}$ and $R^{39}$ have the meanings already mentioned and one or more nonadjacent groups [—$CR^{38}R^{39}$—] can be replaced by oxygen, sulfur or an imino radical optionally substituted by a $C_1$ to $C_5$ alkyl radical and two adjacent groups [—$CR^{38}R^{39}$—] can be replaced by a group [—$CR^{38}$=$CR^{39}$—], $R^{40}$ is identical or different mononuclear radicals selected from the group consisting of a hydrogen, phenyl, aryl-$C_1$–$C_5$-alkyl, $C_1$–$C_{12}$-alkyl, $C_1$–$C_5$-alkoxy and $C_1$–$C_{10}$-carbonyl radical, where phenyl radicals can be unsubstituted or mono- or polysubstituted by a radical $R^{44}$ and the aryl-$C_1$–$C_5$-alkyl, $C_1$–$C_{12}$-alkyl, $C_1$–$C_5$-alkoxy and $C_1$–$C_{10}$-carbonyl radicals can be saturated or unsaturated, branched or unbranched and can be mono- or polysubstituted by a radical $R^{44}$, where $R^{44}$ is identical or different and is a hydroxyl, formyl, cyano or carboxyl radical, ester or salt of the carboxyl radical, carbamoyl, sulfono, sulfamoyl, nitro, nitroso, amino, phenyl, $C_1$–$C_5$-alkyl or $C_1$–$C_5$-alkoxy radical and $R^{41}$ is divalent radicals selected from the group consisting of an ortho-, meta- or para-phenylene, aryl-$C_1$–$C_5$-alkyl, $C_1$–$C_{12}$-alkylene and $C_1$–$C_5$-alkylenedioxy radical, where phenylene radicals can be unsubstituted or mono- or polysubstituted by a radical $R^{44}$ and the aryl-$C_1$–$C_5$-alkyl, $C_1$–$C_{12}$-alkyl and $C_1$–$C_5$-alkoxy radicals can be saturated or unsaturated, branched or unbranched and can be mono- or polysubstituted by a radical $R^{44}$, where p is 0 or 1 and q is an integer from 1 to 3.

$Ar^1$ is preferably a phenyl radical and $Ar^2$ is an ortho-phenylene radical, where $Ar^1$ can be substituted by up to five and $Ar^2$ by up to four identical or different radicals selected from the group consisting of a $C_1$–$C_3$-alkyl, $C_1$–$C_3$-alkylcarbonyl or carboxyl radical, ester or salt of the carboxyl radical, sulfono radical, ester or salt of the sulfono radical, hydroxyl, cyano, nitro, nitroso and amino radical, where amino radicals can be substituted by two different radicals selected from the group consisting of hydroxyl and $C_1$–$C_3$-alkyl-carbonyl.

$R^{40}$ is preferably a monovalent radical selected from the group consisting of a hydrogen, phenyl, $C_1$–$C_{12}$-alkyl and $C_1$–$C_5$-alkoxy radical, where the $C_1$–$C_{12}$-alkyl radicals and $C_1$–$C_5$-alkoxy radicals can be saturated or unsaturated, and branched or unbranched.

$R^{41}$ is preferably divalent radicals selected from the group consisting of an ortho- or para-phenylene, $C_1$–$C_{12}$-alkylene and $C_1$–$C_5$-alkylenedioxy radical, where the aryl-$C_1$–$C_5$-alkyl, $C_1$–$C_{12}$-alkyl and $C_1$–$C_5$-alkoxy radicals can be saturated or unsaturated, branched or unbranched and can be mono- or polysubstituted by a radical $R^{44}$.

$R^{44}$ is preferably a carboxyl radical, ester or salt of the carboxyl radical, carbamoyl, phenyl or $C_1$–$C_3$-alkoxy radical.

Examples of compounds which can be employed as mediators are N-hydroxyacetanilide, N-hydroxypivaloylanilide, N-hydroxyacrylanilide, N-hydroxybenzoylanilide, N-hydroxymethylsulfonylanilide, N-hydroxy-N-phenyl methylcarbamate, N-hydroxy-3-oxobutyrylanilide, N-hydroxy-4-cyanoacetanilide, N-hydroxy-4-methoxyacetanilide, N-hydroxyphenacetin, N-hydroxy-2,3-dimethylacetanilide, N-hydroxy-2-methylacetanilide, N-hydroxy-4-methylacetanilide, 1-hydroxy-3,4-dihydroquinolin-(1H)-2-one, N,N'-dihydroxy-N,N'-diacetyl-1,3-phenylenediamine, N,N'-dihydroxysuccinic dianilide, N,N'-dihydroxymaleic dianilide, N,N'-dihydroxyoxalic dianilide, N,N'-dihydroxyphosphoric dianilide, N-acetoxyacetanilide, N-hydroxymethyloxalylanilide, N-hydroxymaleic monoanilide.

Preferred mediators are N-hydroxyacetanilide, N-hydroxyformanilide, N-hydroxy-N-phenyl methylcarbamate, N-hydroxy-2-methylacetanilide, N-hydroxy-4-methylacetanilide., 1-hydroxy-3,4-dihydroquinolin-(1H)-2-one and N-acetoxyacetanilide.

The mediator can also be selected from the N-alkyl-N-hydroxyamides group.

Mediators preferably employed here are compounds of the general formula (XVII) or (XVIII)

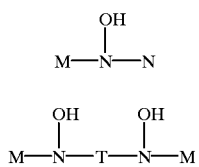

and their salts, ethers or esters, where

M is identical or different and is a monovalent, linear or branched or cyclic or polycyclic, saturated or unsaturated alkyl radical having 1–24 C atoms and where this alkyl radical can be substituted by one or more radicals $R^{45}$, which are identical or different and are selected from the group consisting of a hydroxyl, mercapto, formyl, carbamoyl or carboxyl radical, ester or salt of the carboxyl radical, sulfono radical, ester or salt of the sulfono radical, sulfamoyl, nitro, nitroso, amino, hydroxylamino, phenyl, $C_1$–$C_5$-alkoxy, $C_1$–$C_{10}$-carbonyl, phospho, phosphono or phosphonooxy radical, and ester or salt of the phosphonooxy radical and where carbamoyl, sulfamoyl, amino, hydroxylamino, mercapto and phenyl radicals can be unsubstituted or mono- or polysubstituted by a radical $R^{46}$ and the $C_1$–$C_5$-alkoxy and $C_1$–$C_{10}$-carbonyl radicals can be saturated or unsaturated, branched or unbranched and can be mono- or polysubstituted by a radical $R^{46}$, where $R^{46}$ is identical or different and is a hydroxyl, formyl, cyano or carboxyl radical, ester or salt of the carboxyl radical, carbamoyl, sulfono, sulfamoyl, nitro, nitroso, amino, phenyl, benzoyl, $C_1$–$C_5$-alkyl, $C_1$–$C_5$-alkoxy or $C_1$–$C_5$-alkylcarbonyl radical and methylene groups not in the á-position can be replaced by oxygen, sulfur or an optionally monosubstituted imino radical and N is a monovalent acid radical present in amide form of acids selected from the group consisting of aliphatic or mono- or binuclear aromatic or mono- or binuclear heteroaromatic carboxylic acids having up to 20 C atoms, carbonic acid, hemiesters of carbonic acid or of carbamic acid, sulfonic acid, phosphonic acid, phosphoric acid, monoesters of phosphoric acid and diesters of phosphoric acid and T is a divalent acid radical present in amide form of acids selected from the group consisting of aliphatic, mono- or binuclear aromatic or mono- or binuclear heteroaromatic dicarboxylic acids having up to 20 carbon atoms, carbonic acid, sulfonic acid, phosphonic acid, phosphoric acid and monoesters of phosphoric acid and where alkyl radicals of the aliphatic acids N and T present in amide form can be linear or branched and/or cyclic and/or polycyclic and saturated or unsaturated and comprise zero to 24 carbon atoms and are not substituted or are mono- or polysubstituted by the radical $R^{45}$ and aryl and heteroaryl radicals of the aromatic or heteroaromatic acids N and T present in amide form can be substituted by one or more radicals $R^{47}$, which are identical or different and are selected from the group consisting of a hydroxyl, mercapto, formyl, cyano, carbamoyl or carboxyl radical, ester or salt of the carboxyl radical, sulfono radical, ester or salt of the sulfono radical, sulfamoyl, nitro, nitroso, amino, phenyl, aryl-$C_1$–$C_5$-alkyl, $C_1$–$C_{12}$-alkyl, $C_1$–$C_5$-alkoxy, $C_1$–$C_{10}$-carbonyl, phospho, phosphono or phosphonooxy radical, and ester or salt of the phosphonooxy radical and where carbamoyl, sulfamoyl, amino, mercapto and phenyl radicals can be unsubstituted or mono- or polysubstituted by the radical $R^{46}$ and the aryl-$C_1$–$C_5$-alkyl, $C_1$–$C_{12}$-alkyl-$C_1$–$C_5$-alkoxy and $C_1$–$C_{10}$-carbonyl radicals can be saturated or unsaturated, branched or unbranched and can be mono- or polysubstituted by the radical $R^{46}$.

Particular preferred mediators are compounds of the general formula (XIX), (XX), (XXI) or (XXII):

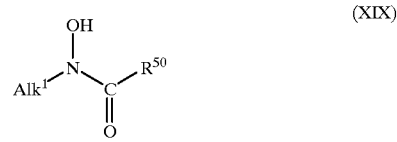

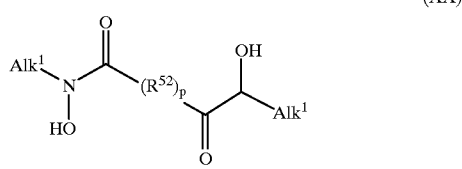

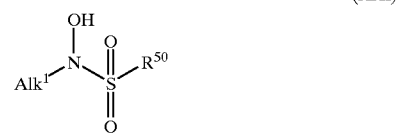

-continued

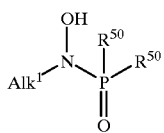

(XXII)

and their salts, ethers or esters, where
Alk¹ is identical or different and is a monovalent, linear or branched or cyclic or polycyclic, saturated or unsaturated alkyl radical having 1–10 C atoms,
where this alkyl radical can be substituted by one or more radicals $R^{48}$, which are identical or different and are selected from the group consisting of a hydroxyl, formyl, carbamoyl or carboxyl radical, ester or salt of the carboxyl radical, sulfono radical, ester or salt of the sulfono radical, sulfamoyl, nitro, nitroso, amino, hydroxylamino, phenyl, $C_1$–$C_5$-alkoxy and $C_1$–$C_5$-carbonyl radicals and where carbamoyl, sulfamoyl, amino, hydroxylamino and phenyl radicals can be unsubstituted or mono- or polysubstituted by a radical $R^{49}$ and the $C_1$–$C_5$-alkoxy and $C_1$–$C_{10}$-carbonyl radicals can be saturated or unsaturated, branched or unbranched and can be mono- or polysubstituted by a radical $R^{49}$, where
  $R^{49}$ is identical or different and is a hydroxyl, formyl, cyano or carboxyl radical, ester or salt of the carboxyl radical, carbamoyl, sulfono, sulfamoyl, nitro, amino, phenyl, benzoyl, $C_1$–$C_5$-alkyl, $C_1$–$C_5$-alkoxy or $C_1$–$C_5$-alkylcarbonyl radical and
methylene groups which are not in the á-position can be replaced by oxygen, sulfur or an optionally monosubstituted imino radical and where
  $R^{50}$ is identical or different monovalent radicals selected from the group consisting of a hydrogen, phenyl, pyridyl, furyl, pyrrolyl, thienyl, aryl-$C_1$–$C_5$-alkyl, $C_1$–$C_{12}$-alkyl, $C_1$–$C_{10}$-alkoxy and $C_1$–$C_{10}$-carbonyl radical,
where phenyl, pyridyl, furyl, pyrrolyl and thienyl radicals can be unsubstituted or mono- or polysubstituted by a radical $R^{51}$ and the aryl-$C_1$–$C_5$-alkyl, $C_1$–$C_{12}$-alkyl, $C_1$–$C_5$-alkoxy and $C_1$–$C_{10}$-carbonyl radicals can be saturated or unsaturated and branched or unbranched and can be mono- or polysubstituted by a radical $R^{51}$ and
  $R^{51}$ is identical or different and is a hydroxyl, formyl or carboxyl radical, ester or salt of the carboxyl radical, carbamoyl, sulfono, sulfamoyl, nitro, amino, phenyl, $C_1$–$C_5$-alkyl or $C_1$–$C_5$-alkoxy radical and
  $R^{52}$ is divalent radicals selected from the group consisting of phenylene, pyridylene, thienylene, furylene, pyrrolylene, aryl-$C_1$–$C_5$-alkyl, $C_1$–$C_{12}$-alkylene and $C_1$–$C_5$-alkylenedioxy radical, where phenylene, pyridylene, thienylene, furylene and pyrrolylene can be unsubstituted or mono- or polysubstituted by a radical $R^{53}$ and the aryl-$C_1$–$C_5$-alkyl, $C_1$–$C_{12}$-alkyl and $C_1$–$C_5$-alkoxy radicals can be saturated or unsaturated and branched or unbranched and can be mono- or polysubstituted by a radical $R^{51}$, where
p is 0 or 1.
Very particularly preferred mediators are compounds having the general formula (XIX)–(XXII), in which
Alk' is identical or different and is a monovalent, linear or branched or cyclic or saturated or unsaturated alkyl radical having 1–10 C atoms,
where this alkyl radical can be substituted by one or more radicals $R^{48}$, which are identical or different and are selected from the group consisting of a hydroxyl, carbamoyl or carboxyl radical, ester or salt of the carboxyl radical, sulfono radical, ester or salt of the sulfono radical, sulfamoyl, amino, phenyl, $C_1$–$C_5$-alkoxy and $C_1$–$C_5$-carbonyl radical and
where carbamoyl, sulfamoyl, amino and phenyl radicals can be unsubstituted or mono- or polysubstituted by a radical $R^{49}$ and the $C_1$–$C_5$-alkoxy and $C_1$–$C_{10}$-carbonyl radicals can be saturated or unsaturated and branched or unbranched and can be mono- or polysubstituted by a radical $R^{49}$, where
  $R^{49}$ is identical or different and is a hydroxyl or carboxyl radical, ester or salt of the carboxyl radical, carbamoyl, sulfono, sulfamoyl, nitro, amino, phenyl, benzoyl, $C_1$–$C_5$-alkyl, $C_1$–$C_5$-alkoxy or $C_1$–$C_5$-alkylcarbonyl radical and where
  $R^{50}$ is identical or different monovalent radicals, selected from the group consisting of a hydrogen, phenyl, furyl, aryl-$C_1$–$C_5$-alkyl, $C_1$–$C_{12}$-alkyl, $C_1$–$C_{10}$-alkoxy and $C_1$–$C_{10}$-carbonyl radical,
where phenyl and furyl radicals can be unsubstituted or mono- or polysubstituted by a radical $R^{51}$ and the aryl-$C_1$–$C_5$-alkyl, $C_1$–$C_{12}$-alkyl, $C_1$–$C_5$-alkoxy and $C_1$–$C_{10}$-carbonyl radicals can be saturated or unsaturated and branched or unbranched and can be mono- or polysubstituted by a radical $R^{51}$, where
  $R^{51}$ is identical or different and is a carboxyl radical, ester or salt of the carboxyl radical, carbamoyl, phenyl, $C_1$–$C_5$-alkyl or $C_1$–$C_5$-alkoxy radical and
  $R^{52}$ is a divalent radical selected from the group consisting of a phenylene, furylene, $C_1$–$C_{12}$-alkylene and $C_1$–$C_5$-alkylenedioxy radical, where phenylene and furanylene can be unsubstituted or mono- or polysubstituted by a radical $R^{51}$ and the aryl-$C_1$–$C_5$-alkyl, $C_1$–$C_{12}$-alkyl and $C_1$–$C_5$-alkoxy radicals can be saturated or unsaturated, branched or unbranched and can be mono- or polysubstituted by a radical $R^{51}$, where
p is 0 or 1.
Examples of compounds which can be employed as mediators are N-hydroxy-N-methylbenzamide, N-hydroxy-N-methylbenzenesulfonamide, N-hydroxy-N-methyl-p-toluenesulfonamide, N-hydroxy-N-methylfuran-2-carboxamide, N-hydroxy-N-methylthiophene-2-carboxamide, N,N'-dihydroxy-N,N'-dimethyl-phthalic diamide, N,N'-dihydroxy-N,N'-dimethylisophthalic diamide, N,N'-dihydroxy-N,N'-dimethylterephthalic diamide, N,N'-dihydroxy-N,N'-dimethylbenzene-1,3-disulfonic diamide, N,N'-dihydroxy-N,N'-dimethylfuran-3,4-dicarboxylic diamide, N-hydroxy-N-tert-butylbenzamide, N-hydroxy-N-tert-butylbenzenesulfonamide, N-hydroxy-N-tert-butyl-p-toluenesulfonamide, N-hydroxy-N-tert-butylfuran-2-carboxamide, N-hydroxy-N-tert-butylthiophene-2-carboxamide, N,N'-dihydroxy-N,N'-di-tert-butylphthalic diamide, N,N'-dihydroxy-N,N'-di-tert-butylisophthalic diamide, N,N'-dihydroxy-N,N'-di-tert-butylterephthalic diamide, N,N'-dihydroxy-N,N'-di-tert-butylbenzene-1,3-disulfonic diamide, N,N'-dihydroxy-N,N'-di-tert-butylfuran-3,4-dicarboxylic diamide, N-hydroxy-N-cyclohexylbenzamide, N-hydroxy-N-cyclohexylbenzenesulfonamide, N-hydroxy-N-cyclohexyl-p-toluenesulfonamide, N-hydroxy-N-cyclohexylfuran-2-carboxamide, N-hydroxy-N-cyclohexylthiophene-2-carboxamide, N,N'-dihydroxy-N,N'-dicyclohexylphthalic diamide, N,N'-dihydroxy-N,N'-dicyclohexylisophthalic diamide, N,N'-dihydroxy-N,N'-dicyclohexylterephthalic diamide, N,N'-dihydroxy-N,N'-dicyclohexylbenzene-1,3-disulfonic diamide, N,N'-dihydroxy-N,N'-dicyclohexylfuran-3,4-dicarboxylic diamide, N-hydroxy-N- isopropylbenzamide, N-hydroxy-N-isopropylbenzenesulfonamide, N-hydroxy-N-isopropyl-p-toluenesulfonamide, N-hydroxy-N-isopropylfuran-2-carboxamide, N-hydroxy-N-isopropylthiophene-2-carboxamide, N,N'-dihydroxy-N,N'-diisopropylphthalic diamide, N,N'-dihydroxy-N,N'-diisopropylisophthalic diamide, N,N'-dihydroxy-N,N'-diisopropylterephthalic diamide, N,N'-dihydroxy-N,N'-diisopropylbenzene-1,3-disulfonic diamide, N,N'-dihydroxy-N,N'-diisopropylfuran-3,4-dicarboxylic diamide, N-hydroxy-N-methylacetamide, N-hydroxy-N-tert-butylacetamide, N-hydroxy-N-isopropylacetamide, N-hydroxy-N-cyclohexylacetamide, N-hydroxy-N-methylpivalamide, N-hydroxy-N-isopropylpivalamide, N-hydroxy-N-methyl-acrylamide, N-hydroxy-N-tert-butylacrylamide, N-hydroxy-N-isopropylacrylamide, N-hydroxy-N-cyclohexylacrylamide, N-hydroxy-N-methylmethanesulfonamide, N-hydroxy-N-isopropylmethanesulfonamide, N-hydroxy-N-isopropyl methylcarbamate, N-hydroxy-N-methyl-3-oxobutyramide, N,N'-di-hydroxy-N,N'-dibenzoylethylenediamine, N,N'-dihydroxy-N,N'-dimethylsuccinic diamide, N,N'-dihydroxy-N,N'-di-tert-butylmaleic diamide, N-hydroxy-N-tert-butylmaleic monoamide, N,N'-dihydroxy-N,N'-di-tert-butyloxalic diamide, tert-butyloxalic diamide, N,N'-dihydroxy-N,N'-di-tert-butyl-phosphoric diamide.

Preferred mediators are compounds selected from the group consisting of N-hydroxy-N-methylbenzamide, N-hydroxy-N-methylbenzenesulfonamide, N-hydroxy-N-methyl-p-toluenesulfonamide, N-hydroxy-N-methylfuran-2-carboxamide, N,N'-dihydroxy-N,N'-dimethylphthalic diamide, N,N'-dihydroxy-N,N'-dimethylterephthalic diamide, N,N'-dihydroxy-N,N'-dimethylbenzene-1,3-disulfonic diamide, N-hydroxy-N-tert-butylbenzamide, N-hydroxy-N-tert-butylbenzenesulfonamide, N-hydroxy-N-tert-butyl-p-toluenesulfonamide, N-hydroxy-N-tert-butylfuran-2-carboxamide, N,N'-dihydroxy-N,N'-di-tert-butylterephthalic diamide, N-hydroxy-N-isopropylbenzamide, N-hydroxy-N-isopropyl-p-toluenesulfonamide, N-hydroxy-N-isopropylfuran-2-carboxamide, N,N'-dihydroxy-N,N'-diisopropylterephthalic diamide, N,N'-dihydroxy-N,N'-diisopropylbenzene-1,3-disulfonic diamide, N-hydroxy-N-methylacetamide, N-hydroxy-N-tert-butylacetamide, N-hydroxy-N-isopropylacetamide, N-hydroxy-N-cyclohexylacetamide, N-hydroxy-N-methylpivalamide, N-hydroxy-N-tert-butylacrylamide, N-hydroxy-N-isopropylacrylamide, N-hydroxy-N-methyl-3-oxobutyramide, N,N'-dihydroxy-N,N'-dibenzoylethylenediamine, N,N'-dihydroxy-N,N'-di-tert-butylmaleic diamide, N-hydroxy-N-tert-butylmaleic monoamide, N,N'-dihydroxy-N,N'-di-tert-butyloxalic diamide.

The mediator can also be selected from the group of oximes of the general formula XXIII or XXIV

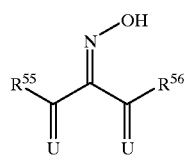

XXIII

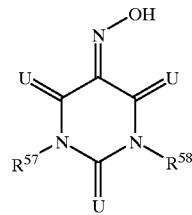

XXIV and their salts, ethers or esters, where

U is identical or different and is O, S or $NR^{53}$, where
  $R^{53}$ is a hydrogen, hydroxyl, formyl, carbamoyl or sulfono radical, ester or salt of the sulfono radical, sulfamoyl, nitro, amino, phenyl, aryl-$C_1$–$C_5$-alkyl, $C_1$–$C_{12}$-alkyl, $C_1$–$C_5$-alkoxy, $C_1$–$C_{10}$-carbonyl, carbonyl-$C_1$–$C_6$-alkyl, phospho, phosphono or phosphonooxy radical, or ester or salt of the phosphonooxy radical, where carbamoyl, sulfamoyl, amino and phenyl radicals can be unsubstituted or mono- or polysubstituted by a radical $R^{54}$ and the aryl-$C_1$–$C_5$-alkyl, $C_1$–$C_{12}$-alkyl, $C_1$–$C_5$-alkoxy, $c_1$–$C_{10}$-carbonyl and carbonyl-$C_1$–$C_6$-alkyl radicals can be saturated or unsaturated and branched or unbranched and can be mono- or polysubstituted by a radical $R^{54}$, where $R^{54}$ is identical or different and is a hydroxyl, formyl or carboxyl radical, ester or salt of the carboxyl radical, carbamoyl or sulfono ester or salt of the sulfono radical, sulfamoyl, nitro, amino, phenyl, $C_1$–$C_5$-alkyl or $C_1$–$C_5$-alkoxy radical and the radicals $R^{55}$ and $R^{56}$ are identical or different and are a halogen or carboxyl radical, or ester or salt of the carboxyl radical, or have the meanings mentioned for $R^{53}$, or are linked to give a ring $[-CR^{59}R^{60}]_n$ where n is equal to 2, 3 or 4 and $R^{57}$ and $R^{58}$ have the meanings mentioned for $R^{53}$ and
  $R^{59}$ and $R^{60}$ are identical or different and are a halogen or carboxyl radical, or ester or salt of the carboxyl radical, or have the meanings mentioned for $R^{53}$.

Particularly preferred mediators are compounds having the general formula XXIII in which U is O or S and the other radicals have the abovementioned meanings. An example of such a compound is dimethyl 2-hydroxyiminomalonate.

Furthermore particularly preferred mediators are isonitroso derivatives of cyclic ureides of the general formula XXIV. Examples of such compounds are 1-methylvioluric acid, 1,3-dimethylvioluric acid, thiovioluric acid and alloxan-4,5-dioxime.

A particularly preferred mediator is alloxan-5-oxime hydrate (violuric acid) and/or its esters, ethers or salts.

The mediator can also be selected from the group consisting of vicinal nitroso-substituted aromatic alcohols of the general formula XXV or XXVI

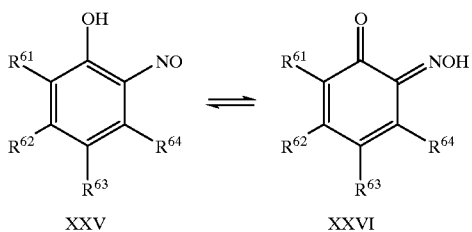

XXV     XXVI and their salts, ethers and esters, where $R^{61}$, $R^{62}$, $R^{63}$ and $R^{64}$ are identical or different and are a hydrogen, halogen, hydroxyl, formyl, carbamoyl or carboxyl radical, ester or salt of the carboxyl radical, sulfono radical, ester or salt of the sulfono radical, sulfamoyl, nitro, nitroso, cyano, amino, phenyl, aryl-$C_1$–$C_5$-alkyl, $C_1$–$C_{12}$-alkyl, $C_1$–$C_5$-alkoxy, $C_1$–$C_{10}$-carbonyl, carbonyl-$C_1$–$C_6$-alkyl, phospho, phosphono or phosphonooxy radical, or ester or salt of the phosphonooxy radical, where carbamoyl, sulfamoyl, amino and phenyl radicals can be unsubstituted or mono- or polysubstituted by a radical $R^{65}$ and the aryl-$C_1$–$C_5$-alkyl, $C_1$–$C_{12}$-alkyl, $C_1$–$C_5$-alkoxy, $C_1$–$C_{10}$-carbonyl and carbonyl-$C_1$–$C_6$-alkyl radicals can be saturated or unsaturated and branched or unbranched and can be mono- or polysubstituted by a radical $R^{65}_1$ where $R^{65}$ is identical or different and is a hydroxyl, formyl or carboxyl radical, ester or salt of the carboxyl radical, carbamoyl, sulfono, sulfamoyl, nitro, nitroso, amino, phenyl, $C_1$–$C_5$-alkyl or $C_1$–$C_5$-alkoxy radical or the radicals $R^{61}$–$R^{64}$ are linked in pairs to give a ring [—$CR^{66}R^{67}$—]$_m$, where m is an integer and is a value from 1 to 4, or are linked to give a ring [—$CR^{68}$=$CR^{69}$—]$_n$, where n is an integer and is a value from 1 to 3, and $R^{66}$, $R^{67}$, $R^{68}$ and $R^{69}$ are identical or different and have the meanings mentioned for $R^{61}$ to $R^{64}$.

Aromatic alcohols are preferably to be understood as meaning phenols or highly condensed derivatives of phenol.

Preferred mediators are compounds of the general formula XXV or XXVI, whose synthesis can be traced back to the nitrosation of substituted phenols. Examples of compounds of this type are 2-nitrosophenol, 3-methyl-6-nitrosophenol, 2-methyl-6-nitrosophenol, 4-methyl-6-nitrosophenol, 3-ethyl-6-nitrosophenol, 2-ethyl-6-nitrosophenol, 4-ethyl-6-nitrosophenol, 4-isopropyl-6-nitrosophenol, 4-tert-butyl-6-nitrosophenol, 2-phenyl-6-nitrosophenol, 2-benzyl-6-nitrosophenol, 4-benzyl-6-nitrosophenol, 2-hydroxy-3-nitrosobenzyl alcohol, 2-hydroxy-3-nitrosobenzoic acid, 4-hydroxy-3-nitrosobenzoic acid, 2-methoxy-6-nitrosophenol, 3,4-dimethyl-6-nitrosophenol, 2,4-dimethyl-6-nitrosophenol, 3,5-dimethyl-6-nitrosophenol, 2,5-dimethyl-6-nitrosophenol, 2-nitrosoresorcinol, 4-nitrosoresorcinol, 2-nitrosoresorcinol, 2-nitrosophloroglucinol and 4-nitrosopyrogallol, 4-nitroso-3-hydroxyaniline, 4-nitro-2-nitrosophenol.

Furthermore preferred mediators are o-nitroso derivatives of more highly condensed aromatic alcohols. Examples of compounds of this type are 2-nitroso-1-naphthol, 1-methyl-3-nitroso-2-naphthol and 9-hydroxy-10-nitrosophenanthrene.

Particularly preferred mediators are 1-nitroso-2-naphthol, 1-nitroso-2-naphthol-3,6-disulfonic acid, 2-nitroso-1-naphthol-4-sulfonic acid, 2,4-dinitroso-1,3-dihydroxybenzene and esters, ethers or salts of the compounds mentioned.

The mediator can also be selected from the group consisting of hydroxypyridines, aminopyridines, hydroxyquinolines, aminoquinolines, hydroxyisoquinolines, aminoisoquinolines with nitroso or mercapto substituents in the ortho- or para-position to the hydroxyl or amino groups, tautomers of the compounds mentioned and their salts, ethers and esters.

Preferred mediators present are compounds of the general formula (XXVII), (XXVIII) or (XXIX)

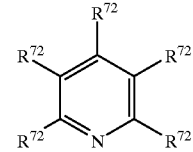
(XXVII)

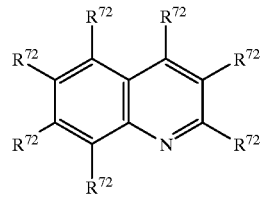
(XXVIII)

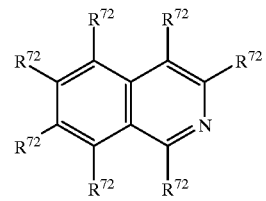
(XXIX)

and tautomers, salts, ethers or esters of the compounds mentioned, where in the formulae XXVII, XXVIII and XXIX two radicals $R^{70}$ which are in the ortho- or para-position to one another are a hydroxyl and nitroso radical or hydroxyl and mercapto radical or nitroso radical and amino radical and the other radicals $R^{70}$ are identical or different and are selected from the group consisting of a hydrogen, halogen, hydroxyl, mercapto, formyl, cyano, carbamoyl or carboxyl radical, ester and salt of the carboxyl radical, sulfono radical, ester and salt of the sulfono radical, sulfamoyl, nitro, nitroso, amino, phenyl, aryl-$C_1$–$C_5$-alkyl, $C_1$–$C_{12}$-alkyl, $C_1$–$C_5$-alkoxy, $C_1$–$C_{10}$-carbonyl, carbonyl-$C_1$–$C_6$-alkyl, phospho, phosphono or phosphonooxy radical, and ester and salt of the phosphonooxy radical and where carbamoyl, sulfamoyl, amino, mercapto and phenyl radicals can be unsubstituted or mono- or polysubstituted by a radical R and the aryl-$C_1$–$C_5$-alkyl, $C_1$–$C_{12}$-alkyl, $C_1$–$C_5$-alkoxy, $C_1$–$C_5$-carbonyl and carbonyl-$C_1$–$C_6$-alkyl radicals can be saturated or unsaturated and branched or unbranched and can be mono- or polysubstituted by a radical $R^{71}$, where $R^{71}$ is identical or different and is a hydroxyl, formyl, cyano or carboxyl radical, ester or salt of the carboxyl radical, carbamoyl, sulfono, sulfamoyl, nitro, nitroso, amino, phenyl, $C_1$–$C_5$-alkyl or $C_1$–$C_5$-alkoxy radical or a $C_1$–$C_5$-alkylcarbonyl radical and each of the two radicals $R^{70}$ or each of the two radicals $R^{71}$ or $R^{70}$ and $R^{71}$ can be linked in pairs via a bridge [—$CR^{72}R^{73}$—]$_m$ where m is equal to 1, 2, 3 or 4 and $R^{72}$ and $R^{73}$ are identical or different and are a carboxyl radical, ester or salt of the carboxyl radical, phenyl, $C_1$–$C_5$-alkyl or $C_1$–$C_5$-alkoxy radical or $C_1$–$C_5$-alkylcarbonyl radical and one or more nonadjacent groups [—CR$^{72}$R$^{73}$—] can be replaced by oxygen, sulfur or an imino radical optionally substituted by C$_1$–C$_5$-alkyl and two adjacent groups [—CR$^{72}$R$^{73}$—] can be replaced by a group (—CR$^2$=R$^{73}$—).

Particularly preferred mediators are compounds of the general formula (XXVII) or (XXVIII) and their tautomers, salts, ethers or esters, where in the formulae (XXVII) and (XXVIII) two radicals R$^{70}$ in the ortho-position to one another are particularly preferably a hydroxyl and nitroso radical or hydroxyl and mercapto radical or nitroso radical and amino radical and the other radicals R$^{70}$ are identical or different and are selected from the group consisting of a hydrogen, hydroxyl, mercapto, formyl, carbamoyl or carboxyl radical, ester and salt of the carboxyl radical, sulfono radical, ester and salt of the sulfono radical, sulfamoyl, nitro, nitroso, amino, phenyl, aryl-C$_1$–C$_5$-alkyl, C$_1$–C$_5$-alkyl, C$_1$–C$_5$-alkoxy, C$_1$–C$_5$-carbonyl, carbonyl-C$_1$–C$_6$-alkyl, phospho, phosphono or phosphonooxy radical, and ester and salt of the phosphonooxy radical where carbamoyl, sulfamoyl, amino, mercapto and phenyl radicals can be unsubstituted or mono- or polysubstituted by a radical R$^{71}$ and the aryl-C$_1$–C$_5$-alkyl, C$_1$–C$_5$-alkyl, C$_1$–C$_5$-alkoxy, C$_1$–C$_5$-carbonyl and carbonyl-C$_1$–C$_6$-alkyl radicals can be saturated or unsaturated and branched or unbranched and can be mono- or polysubstituted by a radical R$^{71}$, where R$^{71}$ has the meanings already mentioned and each of the two radicals R$^{71}$ can be linked in pairs via a bridge [—CR$^{72}$R$^{73}$—]$_m$ where m is equal to 2, 3 or 4 and R$^{72}$ and R$^{73}$ have the meanings already mentioned and one or more nonadjacent groups [—CR$^{72}$R$^{73}$—] can be replaced by oxygen or an imino radical optionally substituted by C$_1$–C$_5$-alkyl.

Examples of compounds which can be employed as mediators are 2,6-dihydroxy-3-nitrosopyridine, 2,3-dihydroxy-4-nitrosopyridine, 2,6-dihydroxy-3-nitrosopyridine-4-carboxylic acid, 2,4-dihydroxy-3-nitrosopyridine, 3-hydroxy-2-mercaptopyridine, 2-hydroxy-3-mercaptopyridine, 2,6-diamino-3-nitrosopyridine, 2,6-diamino-3-nitrosopyridine-4-carboxylic acid, 2-hydroxy-3-nitrosopyridine, 3-hydroxy-2-nitrosopyridine, 2-mercapto-3-nitrosopyridine, 3-mercapto-2-nitrosopyridine, 2-amino-3-nitrosopyridine, 3-amino-2-nitrosopyridine, 2,4-dihydroxy-3-nitrosoquinoline, 8-hydroxy-5-nitrosoquinoline, 2,3-dihydroxy-4-nitrosoquinoline, 3-hydroxy-4-nitrosoisoquinoline, 4-hydroxy-3-nitrosoisoquinoline, 8-hydroxy-5-nitrosoisoquinoline and tautomers of these compounds.

Preferred mediators are 2,6-dihydroxy-3-nitrosopyridine, 2,6-diamino-3-nitrosopyridine, 2,6-dihydroxy-3-nitrosopyridine-4-carboxylic acid, 2,4-dihydroxy-3-nitrosopyridine, 2-hydroxy-3-mercaptopyridine, 2-mercapto-3-pyridinol, 2,4-dihydroxy-3-nitrosoquinoline, 8-hydroxy-5-nitrosoquinoline, 2,3-dihydroxy-4-nitrosoquinoline and tautomers of these compounds.

The mediator can also be selected from the stable nitroxyl radicals (nitroxides) group, i.e. these free radicals can be obtained in pure form, characterized and stored.

Preferred mediators employed here are compounds of the general formula (XXX), (XXXI) or (XXXII)

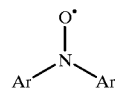 (XXX)

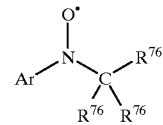 (XXXI)

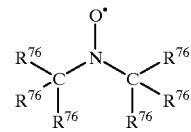 (XXXII)

where
Ar is a monovalent homo- or heteroaromatic mono- or binuclear radical and where this aromatic radical can be substituted by one or more, identical or different radicals R$^{75}$, selected from the group consisting of a halogen, formyl, cyano, carbamoyl or carboxyl radical, ester or salt of the carboxyl radical, sulfono radical, ester or salt of the sulfono radical, sulfamoyl, nitro, nitroso, amino, phenyl, aryl-C$_1$–C$_5$-alkyl, C$_1$–C$_{12}$-alkyl, C$_1$–C$_5$-alkoxy, C$_1$–C$_{10}$-carbonyl, carbonyl-C$_1$–C$_6$-alkyl, phospho, phosphono or phosphonooxy radical, and ester and salt of the phosphonooxy radical and where phenyl, carbamoyl and sulfamoyl radicals can be unsubstituted or mono- or polysubstituted by a radical R$^{76}$, the amino radical can be mono- or disubstituted by R$^{76}$ and the aryl-C$_1$–C$_5$-alkyl, C$_1$–C$_{12}$-alkyl, C$_1$–C$_5$-alkoxy, C$_1$–C$_{10}$-carbonyl and carbonyl-C$_1$–C$_6$-alkyl radicals can be saturated or unsaturated, branched or unbranched and can be mono- or polysubstituted by a radical R$^{76}$, where R$^{76}$ can be present one or more times and is identical or different and is a hydroxyl, formyl, cyano or carboxyl radical, ester or salt of the carboxyl radical, carbamoyl, sulfono, sulfamoyl, nitro, nitroso, amino, phenyl, C$_1$–C$_5$-alkyl, C$_1$–C$_5$-alkoxy or C$_1$–C$_5$-alkylcarbonyl radical and R$^{74}$ is identical or different and is a halogen, hydroxyl, mercapto, formyl, cyano, carbamoyl or carboxyl radical, ester or salt of the carboxyl radical, sulfono radical, ester or salt of the sulfono radical, sulfamoyl, nitro, nitroso, amino, phenyl, aryl-C$_1$–C$_5$-alkyl, C$_1$–C$_{12}$-alkyl, C$_1$–C$_5$-alkoxy, C$_1$–C$_{10}$-carbonyl, carbonyl-C$_1$–C$_6$-alkyl, phospho, phosphono or phosphonooxy radical, or ester or salt of the phosphonooxy radical and R$^{74}$, in the case of bicyclic stable nitroxyl radicals (structure XXXII), can also be hydrogen and where carbamoyl, sulfamoyl, amino, mercapto and phenyl radicals can be unsubstituted or mono- or polysubstituted by a radical R$^{77}$ and the aryl-C$_1$–C$_5$-alkyl, C$_1$–C$_{12}$-alkyl, C$_1$–C$_5$-alkoxy, C$_1$–C$_{10}$-carbonyl and carbonyl-C$_1$–C$_6$-alkyl radicals can be saturated or unsaturated and branched or unbranched and can be mono- or polysubstituted by a radical R$^{77}$, where R$^{77}$ is identical or different and is a hydroxyl, formyl, cyano or carboxyl radical, ester or salt of the carboxyl radical, carbamoyl, sulfono, sulfamoyl, nitro, nitroso, amino, phenyl, C$_1$–C$_5$-alkyl, C$_1$–C$_5$-alkoxy or C$_1$–C$_5$-alkylcarbonyl radical and each of the two radicals R$^{76}$ or R$^{77}$ can be linked in pairs via a bridge [—CR$^{78}$R$^{79}$—]$_m$ where m is equal to 0, 1, 2, 3 or 4 and $R^{78}$ and $R^{79}$ are identical or different and are a halogen or carboxyl radical, ester or salt of the carboxyl radical, carbamoyl, sulfamoyl, phenyl, benzoyl, $C_1$–$C_5$-alkyl, $C_1$–$C_5$-alkoxy or $C_1$–$C_5$-alkylcarbonyl radical and one or more nonadjacent groups [—$CR^{78}R^{79}$—] can be replaced by oxygen, sulfur or an imino radical optionally substituted by $C_1$–$C_5$-alkyl and two adjacent groups [—$CR^{78}R^{79}$—] can be replaced by a group [—$CR^{78}$=$CR^{79}$—], [—$CR^{78}$=N—] or [—$CR^{78}$=N(O)—].

Particularly preferred mediators are nitroxyl radicals of the general formula (XXXIII) and (XXXIV)

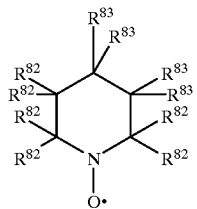

(XXXIII)

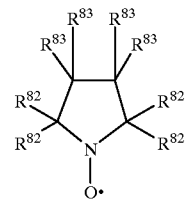

(XXXIV)

where $R^{80}$ is identical or different and is a phenyl, aryl-$C_1$–$C_5$-alkyl, $C_1$–$C_{12}$-alkyl, $C_1$–$C_5$-alkoxy, $C_1$–$C_{10}$-carbonyl or carbonyl-$C_1$–$C_6$-alkyl radical where phenyl radicals can be unsubstituted or mono- or polysubstituted by a radical $R^{82}$ and the aryl-$C_1$–$C_5$-alkyl, $C_1$–$C_{12}$-alkyl, $C_1$–$C_5$-alkoxy, $C_1$–$C_{10}$-carbonyl and carbonyl-$C_1$–$C_6$-alkyl radicals can be saturated or unsaturated and branched or unbranched and can be mono- or polysubstituted by a radical $R^{82}$, where $R^{82}$ can be present one or more times and is identical or different and is a hydroxyl, formyl or carboxyl radical, ester or salt of the carboxyl radical, carbamoyl, sulfono, sulfamoyl, nitro, nitroso, amino, phenyl, benzoyl, $C_1$–$C_5$-alkyl, $C_1$–$C_5$-alkoxy or $C_1$–$C_5$-alkylcarbonyl radical and $R^{81}$ is identical or different and is a hydrogen, hydroxyl, mercapto, formyl, cyano, carbamoyl or carboxyl radical, ester or salt of the carboxyl radical, sulfono radical, ester or salt of the sulfono radical, sulfamoyl, nitro, nitroso, amino, phenyl, aryl-$C_1$–$C_5$-alkyl, $C_1$–$C_{12}$-alkyl, $C_1$–$C_5$-alkoxy, $C_1C_{10}$-carbonyl, carbonyl-$C_1$–$C_6$-alkyl, phospho, phosphono or phosphonooxy radical or ester or salt of the phosphonooxy radical where carbamoyl, sulfamoyl, amino, mercapto and phenyl radicals can be unsubstituted or mono- or polysubstituted by a radical $R^{76}$ and the aryl-$C_1$–$C_5$-alkyl, $C_1$–$C_{12}$-alkyl, $C_1$–$C_5$-alkoxy, $C_1$–$C_{10}$-carbonyl and carbonyl-$C_1$–$C_6$-alkyl radicals can be saturated or unsaturated and branched or unbranched and can be mono- or polysubstituted by a radical $R^{76}$ and a [—$CR^{81}R^{81}$—] group can be replaced by oxygen, an imino radical optionally substituted by $C_1$–$C_5$-alkyl, a (hydroxy)imino radical, a carbonyl function or a vinylidene function optionally mono- or disubstituted by $R^{76}$ and two adjacent groups [—$CR^{81}R^{81}$—] can be replaced by a group [—$CR^{81}$=$CR^{81}$—] or [—$CR^{81}$=N—] or [—$CR^{81}$=N(O)—].

Examples of compounds which can be employed as mediators are 2,2,6,6-tetramethylpiperidin-1-oxyl (TEMPO),
4-hydroxy-2,2,6,6-tetramethylpiperidin-1-oxyl,
4-oxo-2,2,6,6-tetramethylpiperidin-1-oxyl,
4-acetamido-2,2,6,6-tetramethylpiperidin-1-oxyl,
4-(ethoxyfluorophosphinyloxy)-2,2,6,6-tetramethyl-piperidin-1-oxyl,
4-(isothiocyanato)-2,2,6,6-tetramethylpiperidin-1-oxyl,
4-maleimido-2,2,6,6-tetramethylpiperidin-1-oxyl,
4-(4-nitrobenzoyloxy)-2,2,6,6-tetramethylpiperidin-1-oxyl,
4-(phosphonooxy)-2,2,6,6-tetramethylpiperidin-1-oxyl,
4-cyano-2,2,6,6-tetramethylpiperidin-1-oxyl,
3-carbamoyl-2,2,5,5-tetramethyl-3-pyrrolin-1-oxyl,
4-phenyl-2,2,5,5-tetramethyl-3-imidazolin-3-oxide-1-oxyl,
4-carbamoyl-2,2,5,5-tetramethyl-3-imidazolin-3-oxide-1-oxyl,
4-phenacylidene-2,2,5,5-tetramethylimidazolidin-1-oxyl,
3-(aminomethyl)-2,2,5,5-tetramethylpyrrolidin-N-oxyl,
3-carbamoyl-2,2,5,5-tetramethylpyrrolidin-N-oxyl,
3-carboxyl-2,2,5,5-tetramethylpyrrolidin-N-oxyl,
3-cyano-2,2,5,5-tetramethylpyrrolidin-N-oxyl,
3-maleimido-2,2,5,5-tetramethylpyrrolidin-N-oxyl,
3-(4-nitrophenoxycarbonyl)-2,2,5,5-tetramethylpyrrolidin-N-oxyl.

Preferred mediators are 2,2,6,6-tetramethylpiperidin-1-oxyl (TEMPO),
4-hydroxy-2,2,6,6-tetramethylpiperidin-1-oxyl,
4-oxo-2,2,6,6-tetramethylpiperidin-1-oxyl,
4-acetamido-2,2,6,6-tetramethylpiperidin-1-oxyl,
4-(isothiocyanato)-2,2,6,6-tetramethylpiperidin-1-oxyl,
4-maleimido-2,2,6,6-tetramethylpiperidin-1-oxyl,
4-(4-nitrobenzoyloxy)-2,2,6,6-tetramethylpiperidin-1-oxyl,
4-(phosphonooxy)-2,2,6,6-tetraethylpiperidin-1-oxyl,
4-cyano-2,2,6, 6-tetramethylpiperidin-1-oxyl,
3-carbamoyl-2,2,5,5-tetramethyl-3-pyrrolin-1-oxyl,
4-phenyl-2,2,5,5-tetramethyl-3-imidazolin-3-oxide-1-oxyl,
4-carbamoyl-2,2,5,5-tetramethyl-3-imidazolin-3-oxide-1-oxyl,
4-phenacylidene-2,2,5,5-tetramethyl-imidazolidin-1-oxyl.

Particularly preferred mediators are
2,2,6,6-tetramethylpiperidin-1-oxyl (TEMPO), and
4-hydroxy-2,2,6,6-tetramethylpiperidin-1-oxyl.

The avoidance of a harmful mediator effect on the entire system can also be achieved by using a hydrolase of the enzyme class 3.2.1 which, compared with a modification by activated mediator, shows no disadvantageous change in its enzymatic properties for the described use (e.g. a mediator-resistant xylanase or cellulase).

The multicomponent system or composition according to the invention includes at least one enzymatically active additive selected from the hydrolases group of the enzyme class 3.2.1.

The hydrolases of the enzyme class 3.2.1 are preferably hemicellulases, e.g. xylanases, mannanases or cellulases.

The enzymatically active additive is particularly preferably an endo 1,4-â-xylanase (enzyme class 3.2.1.8) and/or an endo 1,4-á-glucanase (enzyme class 3.2.1.4).

The hydrolases of the enzyme class 3.2.1 are commercially available or can be obtained by standard processes. The hydrolases of the enzyme class 3.2.1 can either be obtained from the natural organisms or produced in suitable expression systems by means of known recombinant DNA technology and isolated from the culture medium according to the prior art. Suitable organisms for the production of these enzymes are, for example, plants, animal cells, bacteria and fungi. In principle, both naturally occurring and genetically modified organisms can be enzyme producers. Likewise, parts of monocellular or multicellular organisms are conceivable as enzyme producers, especially cell cultures.

The hydrolases of the enzyme class 3.2.1 can have also been modified by known molecular biology processes in such a manner that they are suitable for the described use, e.g. by rendering them insensitive to the activated mediator or to a proteolytic activity.

The invention also relates to processes for the delignification of lignin-containing materials, which comprises mixing at least one oxidoreductase and at least one oxidant suitable for the oxidoreductase and at least one mediator which does not inactivate an enzyme selected from the oxidoreductases and hydrolases group of the enzyme class 3.2.1. and mixing at least one endohydrolase simultaneously or in any desired sequence with an aqueous suspension of the lignin-containing material.

Surprisingly, it is possible in the process according to the invention to combine the oxidative delignifier system of laccase and a mediator substance with a hydrolytic enzyme, such as, for example, the xylanase and/or the cellulase, in a single process step.

This is all the more surprising, as it is known that when using HBT as a mediator the activity of the laccase itself is adversely affected (Amann, 1997) and simultaneously present enzymes are irreversibly damaged and thus exhibit greatly decreased activity (Oksanen, 1997).

The process according to the invention has the following advantages:

It improves the bleachability of pulp

It can be combined with established chemical process stages without problems.

For example, even in combination with customary process steps from pulp production, e.g. an alkaline extraction, lignin can be removed selectively from the material employed.

For the process according to the invention, for example, lignin-containing material of plant origin is used, preferably that which was broken down using the process customary for mechanical pulp or pulp production.

The material employed can be unbleached pulp or material which has already been treated using chemical delignification and bleaching processes.

In the process according to the invention, 0.1–100 IU of oxidoreductase are preferably employed per g of lignin-containing material (dry weight), particularly preferably 0.5–20 IU per g of lignin-containing material.

The concentration of the oxidant is preferably in the range from 0.001 to 50 mmol/l. If hydrogen peroxide is employed as an oxidant, then it is preferably in the range from 0.001–25 mmol/l.

The mediator is preferably employed in amounts of 1–500 mmol/kg of pulp, particularly preferably in amounts of 5–300 mmol/kg of pulp, in particular in amounts of 10–200 mmol/kg of pulp (abs. dry—absolutely dry).

In the process according to the invention, cellulases and/or hemicellulases are preferably used as enzymatic additives. For example, cellulase, xylanases or mannanases can be used in pure form or in the form of mixtures. Xylanases are already used in the processing of pulps and are supplied by several manufacturers, e.g. Novo-Nordisk (Pulpzyme®), Clariant (Cartazyme®). Cellulases are also commercially available.

Depending on the conditions which are set in the process according to the invention for enzymatic delignification, correspondingly highly suitable variants (pH optimum, temperature stability) of these enzymes can be used.

In the process according to the invention, the hydrolase of the enzyme class 3.2.1 is used in dosages of 0.01–1000 IU of enzyme/g of pulp, preferably in dosages of 1–500 IU of enzyme/g, particularly preferably in dosages of 5–100 IU/g of pulp (abs. dry—absolutely dry).

Hemicellulases are preferably used in dosages of 0.1–1000 IU of enzyme/g of pulp, preferably in dosages of 1–500 IU of enzyme/g, particularly preferably in dosages of 5–100 IU/g of pulp (abs. dry—absolutely dry).

Cellulases are preferably used in dosages of 0.01–500 IU of enzyme/g of pulp, preferably 0.05–100 IU of enzyme/g of pulp, particularly preferably 0.1–10 IU of enzyme/g of pulp.

Customarily, the process according to the invention is carried out at temperatures between 40 and 90° C., preferably between 45 and 70° C., particularly preferably between 45 and 65° C.

Depending on the temperature stability of the enzymes used, optimal reaction conditions which are different from these can be set. In general, good delignification results can be achieved in the pH range from pH 3–pH 10, and the pH range of pH 4.5–7 is particularly preferred.

When using laccases, adequate availability of dissolved oxygen is a necessary condition. Depending on the temperature selected, the adequate oxygen concentration can be guaranteed by applying a sufficiently high pressure to the system. The necessary oxygen partial pressure can either be already guaranteed by the hydrostatic pressure or can be achieved by applying a suitable pressure by means of a suitable, oxygen-containing gas mixture, such as, for example, air or alternatively pure oxygen gas.

The customary pressure range lies in the range of an oxygen partial pressure ($PO_2$) of 0.1–20 bar, preferably in the pressure range from 0.3–10 bar.

Depending on the choice of mediator, the enzyme dosages and the reaction conditions, the process can proceed at different rates. The customary reaction time is between 30 min and 2 hours.

The pulp concentration (pulp density) of the process according to the invention customarily lies in the range from 1–25%, preferably in the range from 6–20%, particularly preferably in the range 10–15%.

DETAILED DESCRIPTION OF PREFERRED EMBODIMENTS

The invention is described further in the following examples.

The following components are employed in the examples:
Mediators

Mediators were obtained from Aldrich, Merck or Janssen or prepared by customary and generally known processes. Some mediators are designated by abbreviations in the text as follows: 1-OH-benzotriazole (HBT), violuric acid (VIO), N—OH-acetanilide (NHA).
Enzymes
Laccase Laccase obtained from Trametes versicolor by fermentation was used.
Activity Determination Laccase activity is determined under aerobic conditions by means of the oxidation of 2,2'-azinobis(3-ethylbenzothiazoline-6-sulfonate), ABTS, Boehringer Mannheim. The green color which is formed by the enzymatic reaction is measured photometrically at 420 nm. The reaction temperature is 25° C., the pH 4.5. One laccase unit is the amount of enzyme which catalyzes the conversion of 1 mol of ABTS/min under the conditions indicated. For calculation of the conversion, an extinction coefficient of 36,000 $M^{-1}cm^{-1}$ is used.

Cellulose

Commercially available celluloses from Fluka (*Trichoderma viride*), Sigma (*Aspergillus niger, Trichoderma viride, Penicillium funiculosum*), Röhm (Rohalase 7069) were used. The dosage was carried out according to the activity details of the manufacturer.

Xylanase

Commercially available xylanases from Fluka (*Trichoderma viride*) or Clariant were used. The dosage was carried out according to the activity details of the manufacturer.

Pulps

Hardwood (HW) and softwood (SW) kraft pulp were used.

Softwood: kappa 14.5 (after extraction)

Hardwood: kappa 12 (after extraction)

The delignification was assessed by determination of the kappa value (according to TAPPI method T236) of the treated pulp sample after alkaline extraction. Alkaline extraction (E stage) was carried out at 2% pulp density, 60° C. using 80 g of NaOH/kg of pulp and a time of 60 min.

EXAMPLE 1

Comparison of the delignification of an SW pulp using a laccase mediator system (LMS®) with simultaneous presence/absence of xylanase.

In a 500 ml laboratory autoclave, the batch described in the table below was incubated for two hours at 45° C. (water bath) with application of an oxygen partial pressure of 10 bar (L stage).

L Stage 5 g of softwood pulp (abs. dry)

Pulp density: 10%

Laccase: 5 IU/g of pulp

Mediator: N—OH-acetanilide: 9 mg/g of pulp pH: 4.5

Total liquid volume: 50 ml

In order to determine the positive effect of an enzymatic additive, such as, for example, xylanase, xylanase from *Trichoderma viride* (Fluka) was added to the described L stage as a further additive (XL stage), such that the batch had the following composition:

(XL) Stage 5 g of softwood pulp (abs. dry)

Substance density: 10%

Laccase: 5 IU/g of pulp

Xylanase: 50 IU/g of pulp

Mediator: N—OH-acetanilide: 9 mg/g of pulp pH: 4.5

Total liquid volume: 50 ml

Both batches were then extracted under alkaline conditions for 60 min (E stage).

E Stage

2% pulp density

Temperature: 60° C.

Alkali: 80 g of NaOH/kg of pulp

The degree of delignification was determined from the determination of the kappa values. The control value indicates the kappa value of the starting pulp after alkaline extraction.

TABLE 1

EXPERIMENTAL EVALUATION

| Treatment | Kappa value | Delignification |
|---|---|---|
| Control E | 14.5 | 0 |
| LE (PA) | 10.9 | 25% |
| (XL) E | 9.8 | 32.4% |

(PA = experiment according to the prior art/comparison experiment)

The addition of xylanase increases the delignification by about 30%.

EXAMPLE 2

Comparison of the delignification of an HW pulp using a laccase mediator system (LMS®) with simultaneous presence/absence of xylanase.

The example corresponds to Example 1 with the difference that instead of softwood pulp a hardwood pulp was used. In a 500 ml laboratory autoclave, the batch described in the table below was incubated for two hours at 45° C. (water bath) with application of an oxygen partial pressure of 10 bar (L stage)

L Stage 5 g of hardwood pulp (abs. dry)

Pulp density: 10%

Laccase: 5 IU/g of pulp

Mediator: N—OH-acetanilide: 6 mg/g of pulp pH: 4.5

Total liquid volume: 50 ml

In order to determine the positive effect of an enzymatic additive, such as, for example, xylanase, xylanase from *Trichoderma viride* (Fluka) was added to the described L stage as a further additive (XL stage), such that the batch had the following composition:

(XL) Stage 5 g of softwood pulp (abs. dry)

Substance density: 10%

Laccase: 5 IU/g of pulp

Xylanase: 50 IU/g of pulp

Mediator: N—OH-acetanilide: 9 mg/g of pulp pH: 4.5

Total liquid volume: 50 ml

The batches were then extracted under alkaline conditions for 60 min (E stage).

E Stage

2% pulp density

Temperature: 60° C.

Akali: 80 g of NaOH/kg of pulp

The degree of delignification was determined from the determination of the kappa values. The control value indicates the kappa value of the starting pulp after alkaline extraction.

TABLE 2

EXPERIMENTAL EVALUATION

| Treatment | Kappa value | Delignification |
|---|---|---|
| Control E | 12 | 0 |
| LE (PA) | 10.3 | 14% |
| (XL) E | 8.7 | 27.5% |

The addition of xylanase increases the delignification by about 96%.

EXAMPLE 3

Effects of various xylanases on the delignification of a pulp using a laccase mediator system (LMS®).

In order to investigate the effects of the addition of different xylanases, the delignification effect corresponding to the (XL) stage described in Example 1 was investigated using different xylanases. The xylanases used were:

Clariant: Cartazym HS 10, liquid

Fluka: *Trichoderma viride* xylanase

L and (XL) stages were carried out according to Example 1, but the batches were conducted at pH 6.0. The xylanase dosage was in each case 12 IU/g of pulp, laccase was dosed at 15 IU/g of pulp.

The batches were then extracted under alkaline conditions for 60 min (E stage, Example 1). The degree of delignification was determined from the determination of the kappa values.

TABLE 3

RESULTS

| Xylanase used | Kappa value | Delig. (%) |
|---|---|---|
| None (PA) | 11.3 | 21.8 |
| Clariant "Cartazym" | 11 | 24.1 |
| Fluka "*Trichoderma viride*" | 9.6 | 33.6 |

In order to achieve optimum delignification, the best combinations of pulp, LMS and xylanase have to be determined. As the example shows, different xylanases lead to varyingly good delignifications. All results, however, are better than without xylanase.

EXAMPLE 4

Mediator dependence of the delignification using a laccase mediator system (LMS®) with simultaneous presence of xylanase.

In order to determine the effect of the mediator on the system, the delignification effect of the (XL) stage described in Example 1 was investigated using different mediators.

The mediators used were (abbreviations in brackets); 1-OH-benzotriazole (HBT), violuric acid (Vio), N—OH-acetanilide (NHA), —OH-phthalimide (HPI), disodium 1-nitroso-2-naphthol-3,6-disulfonate hydrate (1-NNS), 2-nitroso-1-naphthol-4-sulfonic acid tetrahydrate (2-NNS).

The batches were carried out as in Example 1. In detail, they contained:

(XL) Stage (Mediator Dependence)

5 g of softwood pulp (abs. dry)

Pulp density: 10%

Laccase: 15 IU/g of pulp

Xylanase (Trichoderma): 25 IU/g of pulp

Mediators: 75 mmol/kg of pulp pH: 6.0

Total liquid volume: 50 ml

The batches were then extracted under alkaline conditions for 60 min (E stage), as described in Example 1. The degree of delignification (delig.) was determined from the determination of the kappa values. The control value indicates the kappa value of the starting pulp after alkaline extraction.

TABLE 4

EXPERIMENTAL EVALUATION

| Mediator | Kappa value without xyl | Delig. (%) without xyl | Kappa value with xyl | Delig. (%) with xyl | Increase in delignification (without xyl/with xyl) |
|---|---|---|---|---|---|
| without (ctrl.) | 14.5 | 0 | 14.5 | 0 | 0% |
| HBT (PA) | 12.2 | 15.9 | 11.6 | 20 | 5.0% |
| Vio | 12.5 | 13.8 | 10.5 | 27.6 | 19.0% |
| NHA | 10.6 | 26.9 | 9 | 37.9 | 17.8% |
| 1-NNS | 10.8 | 25.5 | 8.8 | 39.3 | 22.7% |
| 2-NNS | 10.5 | 27.6 | 8.8 | 39.3 | 19.3% |
| HPI | 13.3 | 8.3 | 11.5 | 20.6 | 15.6% | xyl: xylanase

The xylanase effect depends strongly on the mediator used. While the delignification when using 1-OH-benzotriazole (HBT) hardly increases (+5%), significant increases can be observed with other mediators (Ex. NHA +17.8%).

EXAMPLE 5 pH dependence of the delignification of a pulp using a laccase mediator system (LMS®) with simultaneous presence of xylanase.

In order to determine the effect of pH on the system, the delignification effect of the (XL) stage described in Example 1 was investigated at different pHs. The comparisons used were corresponding batches without xylanase (L stage). The batches were carried out as in Example 1. In detail, they contained:

(XL) Stage—(pH Dependence)

5 g of softwood pulp (abs. dry)—kappa 14.5

Pulp density: 10%

Laccase: 15 IU/g of pulp

Xylanase (*Trichoderma viride*): 25 IU/g of pulp

Mediator: N—OH-acetanilide: 9 mg/g of pulp pHs: 4/5/6/7 (using McIllvaine buffer)

Total liquid volume: 50 ml

Both batches were then extracted under alkaline conditions for 60 min (E stage).

The degree of delignification was determined from the determination of the kappa values.

TABLE 5

EXPERIMENTAL EVALUATION

| pH | Kappa value (K) without xyl | Delignification without xyl | Kappa value (K) with xyl | Delignification with xyl |
|---|---|---|---|---|
| 4 | 11.3 | 22% | 10 | 31% |
| 5 | 11 | 24% | 9.3 | 36% |
| 6 | 10 | 31% | 8.5 | 41% |
| 7 | 12.4 | 14.5% | 11.2 | 23% |

A drastic improvement in performance can be achieved by the addition of xylanase to the laccase mediator system. The effect shows a marked pH dependence. However, an improvement can be achieved at all pHs by the addition of xylanase.

EXAMPLE 6

Dependence of the delignification of a pulp using a laccase mediator system (LMS®) with simultaneous presence of a differing amount of xylanase (dose dependence).

In order to determine the effect of the xylanase dosage on the system, the delignification effect of the (XL) stage described in Example 1 was investigated with differing xylanase dosages. The comparison used was a corresponding batch without xylanase (L stage). The batches were carried out as in Example 1. In detail, they contained:

L Stage (reference value without xylanase)
5 of softwood pulp (abs. dry)
Pulp density: 10%
Laccasse: 5 IU/g of pulp
Mediator: N—OH-acetanilide: 9 mg/g of pulp
pH: 4.5
Total liquid volume: 50 ml XL) Stage—(varying amounts of xylanase)
5 g of softwood pulp (abs. dry)—kappa 14.5
Pulp density: 10%
Laccase: 5 IU/g of pulp
Xylanase (*Trichoderma viride*):
12.5/25/37.5/50/100/200 IU/g of pulp
Mediator: N—OH-acetanilide: 11 mg/g of pulp
pH: 4.5
Total liquid volume: 50 ml After the incubation, the batches were extracted under alkaline conditions for 60 min (E stage).

The degree of delignification was determined from the determination of the kappa values.

TABLE 6

EXPERIMENTAL EVALUATION

| Xylanase dosage (IU/g) | Kappa value | Delignification | Relative increase in delignification |
|---|---|---|---|
| 0 | 10 | 31% | — |
| 6.3 | 9.3 | 36% | 16% |
| 12.5 | 8.4 | 42% | 35% |
| 25 | 8.5 | 41% | 32% |
| 37.5 | 8.9 | 39% | 26% |
| 50 | 10.1 | 30% | −3% |
| 100 | 10 | 31% | 0% |
| 200 | 10.2 | 30% | −3% |

The improvement in the effectiveness of the laccase mediator system is dependent on the dose of xylanase added.

EXAMPLE 7

Delignification of an SW pulp using a laccase mediator system (LMS®) which contains cellulase as an additive.

In a 500 ml laboratory autoclave, the reference batch described in the table below was incubated for 2 hours at 45° C. (water bath) with application of an oxygen partial pressure of 10 bar (L stage).

L Stage (comparison experiment)
5 g of softwood pulp (abs. dry)
Pulp density: 10%
Laccase: 15 IU/g of pulp
Mediator: N—OH-acetanilide: 10 mg/g of pulp
pH: 4.5
Total liquid volume: 50 ml In order to determine the positive effect of an enzymatic additive, such as, for example, cellulase, cellulase from *Trichoderma viride* (Sigma) was added to a batch corresponding to the L stage as a further additive (CL stage), such that the batch had the following composition:

(CL) Stage
5 g of softwood pulp (abs. dry)
Pulp density: 10%
Laccase: 15 IU/g of pulp
Cellulase: 10 U/g of pulp
Mediator: N—OH-acetanilide: 10 mg/g of pulp
pH: 4.5
Total liquid volume: 50 ml Both batches were then extracted under alkaline conditions for 60 min (E stage).

E Stage
2% pulp density
Temperature: 60° C.
Alkali: 80 g of NaOH/kg of pulp

The degree of delignification was determined from the determination of the kappa values of both batches. The control value indicates the kappa value of the starting pulp after alkaline extraction.

TABLE 7

EXPERIMENTAL EVALUATION

| Treatment | Kappa value | Delignification |
|---|---|---|
| Control E | 16.6 | 0 |
| (CL) E | 11 | 33.7% |

The addition of cellulase increases the delignification of a softwood pulp in comparison with a cellulase-free reference by 43%.

EXAMPLE 8

Delignification of an HW pulp using a laccase mediator system (LMS®) which contains cellulase as an additive.

In a 500 ml laboratory autoclave, the reference batch described in the table below was incubated for 2 hours at 45° C. (water bath) with application of an oxygen partial pressure of 10 bar (L stage).

L Stage (comparison experiment)
5 g of hardwood pulp (abs. dry)
Pulp density: 10%
Laccase: 15 IU/g of pulp
Mediator: N—OH-acetanilide: 10 mg/g of pulp
pH: 4.5
Total liquid volume: 50 ml In order to determine the positive effect of an enzymatic additive, such as, for example, cellulase, cellulase from *Trichoderma viride* (Sigma) was added to a batch corresponding to the L stage as a further additive (CL stage), such that the batch had the following composition:

(CL) Stage
5 g of hardwood pulp (abs. dry)
Pulp density: 10%
Laccase: 15 IU/g of pulp
Cellulase: 10 U/g of pulp
Mediator: N—OH-acetanilide: 10 mg/g of pulp
pH: 4.5
Total liquid volume: 50 ml Both batches were then extracted under alkaline conditions for 60 min (E stage).

E Stage
2% pulp density
Temperature: 60° C.
Alkali: 80 g of NaOH/kg of pulp

The degree of delignification was determined from the determination of the kappa values of both batches. The control value indicates the kappa value of the starting pulp after alkaline extraction.

TABLE 8

EXPERIMENTAL EVALUATION

| Treatment | Kappa value | Delignification |
|---|---|---|
| Control E | 12 | 0% |
| LE | 10.5 | 12.4% |
| (CL) E | 8.9 | 25.8% |

The addition of cellulase increases the delignification of a hardwood pulp in comparison with a cellulase-free reference by 108%.

EXAMPLE 9

Effect on the cellulase activity by the laccase mediator system (LMS®) when using different mediators.

An effect on the delignificability of pulp can only be observed if the cellulase is enzymatically active in the presence of the laccase mediator system. The activity of cellulases was therefore measured in a pulp-free system which contained laccase and mediator. Cellulase from *Aspergillus niger* and *Trichoderma viride* was investigated. The mediators used were 1-OH-benzotriazole (HBT), violuric acid (Vio) and N—OH-acetanilide (NHA). The cellulase activity was measured in an optical test using dinitrosalicylic acid (DNSA) as an oxidant as described below.

Batches

The batches contained, in a total volume of 10 ml, 20 mg of cellulase, 0.8 mg of laccase and 75 ìmol of mediator at a pH of 6.2. 50 ìl each of the batch were taken after different times and the cellulase activity was determined.

Cellulase Test

Principle: determination of the amount of reducing sugar which is released by the enzymatic hydrolysis of carboxymethylcellulose (CMC). A subsequent redox reaction between added DNSA and the enzymatically formed reducing sugar terminals leads to a coloration of the solution which can be quantified photometrically at 595 nm.

For the enzyme test, 325 µl of test buffer (0.1 mol/l citrate/phosphate pH 6.2 with 0.4 mol/l NaCl), 125 µl of CMC solution (2% in test buffer; Na salt) and 50 µl of the cellulase-containing solution to be tested are pipetted together and incubated at 45° C. for different times. After completion of the incubation, 750 µl of DNSA solution (dissolve 1 g of 3,5-dinitrosalicylic acid, 0.2 g of phenol, 0.05 g of $Na_2SO_3$ and 20 of NaK tartrate in 100 ml of 1% strength NaOH) are added to each batch and the mixture is then heated at 95° C. for 20 min. The solution is cooled on ice, material possibly precipitating is centrifuged off (2 min, 14,000 rpm, Eppendorf centrifuge) and the extinction at 595 nm is determined in the supernatant. By comparison with a calibration curve (glucose), the formation of reducing sugars can be quantified. 1 unit (1U) here designates that enzyme activity which in 1 minute releases 1 µmol of glucose from CMC-cellulose under the conditions indicated.

TABLE 9

Time dependence of the cellulase activity of *Aspergillus niger* in the presence of the laccase mediator system when using various mediators (HBT, NHA, Vio). The numbers indicate the relative cellulase activity in percent of the starting value (rel %).

| Time (min) | NHA | HBT | Vio |
|---|---|---|---|
| 0 | 100 | 100 | 100 |
| 30 | 81 | 49 | 43 |
| 60 | 65 | 38 | 39 |
| 120 | 47 | 40 | 40 |
| 170 | 45 | 43 | 38 |
| 1300 | 43 | 42 | 41 |

TABLE 10

Time dependence of the cellulase activity of *Trichoderma viride* in the presence of the laccase mediator system when using various mediators (HBT, NHA, Vio). The numbers indicate the relative cellulase activity in percent of the starting value (rel %).

| Time (min) | NHA | HBT | Vio |
|---|---|---|---|
| 0 | 100 | 100 | 100 |
| 60 | 95 | 96 | 95 |
| 120 | 92 | 82 | 91 |
| 170 | 77 | 75 | 64 |
| 1300 | 70 | 33 | 18 |

The enzymatic activity of the cellulases from *A. niger* and *T. viride* decreases on simultaneous incubation in the laccase mediator system. The smallest losses are found using NHA as a mediator. A dependence on the enzyme used can likewise be observed.

EXAMPLE 10

Delignification of an SW pulp using a laccase mediator system (LMS®) which contains cellulase of differing origin as an additive.

In a 500 ml laboratory autoclave, the reference batch described in the table below was incubated for 2 hours at 45° C. (water bath) with application of an oxygen partial pressure of 10 bar (L stage).

L Stage (Comparison Experiment)
  5 g of softwood pulp (abs. dry)
  Pulp density: 10%
  Laccase: 15 IU/g of pulp
  Mediator: N—OH-acetanilide: 10 mg/g of pulp
  pH: depending on cellulase, pH 5–6 (table)
  Total liquid volume: 50 ml In order to determine the positive effect of an enzymatic additive, such as, for example, cellulase, cellulase of differing manufacturers was added to a batch corresponding to the L stage as a further additive (CL stage), such that the batch had the following composition:

(CL) Stage
  5 g of softwood pulp (abs. dry)
  Pulp density: 10%
  Laccase: 15 IU/g of pulp
  Cellulase (varying origin): 10 U/g of pulp
  Mediator: N—OH-acetanilide: 10 mg/g of pulp
  pH: depending on the cellulase, pH 5–6 (Table 11)
  Total liquid volume: 50 ml Both batches were then extracted under alkaline conditions for
  60 min (E stage).

E Stage
  2% pulp density
  Temperature: 60° C.
  Alkali: 80 g of NaOH/kg of pulp The degree of delignification was determined from the determination of the kappa values. The control value indicates the kappa value of the starting pulp after alkaline extraction.

TABLE 11

EXPERIMENTAL EVALUATION

Improvement in delignification using the laccase mediator system with simulataneous presence of cellulases of differing origin

| Cellulase | Company | pH | Delignification (%) | Increase compared with control (%) |
|---|---|---|---|---|
| None (control) | — | pH 5 | 23.5 | 0 |
| Aspergillus niger | Sigma | pH 5 | 26.0 | 10 |
| Trichoderma viride | Sigma | pH 6 | 33.7 | 43 |
| Penicillium funicolosum | Sigma | pH 6 | 31.3 | 33 |
| Rohalase 7069 | Röhm | pH 6 | 32.5 | 38 |

With all cellulases used, the delignification efficiency of the laccase mediator system can be improved.

EXAMPLE 11

Effect of the cellulose dose on delignification by means of a laccase mediator system (LMS®) which contains cellulase as an additive.

In a 500 ml laboratory autoclave, the reference batch described in the table below was incubated for 2 hours at 45° C. (water bath) with application of an oxygen partial pressure of 10 bar (L stage).

L Stage (Comparison Experiment)
  5 g of softwood pulp (abs. dry)
  Pulp density: 10%
  Laccase: 15 IU/g of pulp
  Mediator: N—OH-acetanilide: 10 mg/g of pulp
  pH: pH 6
  Total liquid volume: 50 ml In order to determine the positive effect of the enzymatic additive (cellulase), various amounts of cellulase were added to a batch corresponding to the L stage as a further additive (CL stage), such that the batch had the following composition:

(CL) Stage
  5 g of softwood pulp (abs. dry)
  Pulp density: 10%
  Laccase: 15 IU/g of pulp
  Cellulase (Trichoderma viride—Sigma) 0–30 U/g of pulp
  Mediator: N—OH-acetanilide: 10 mg/g of pulp
  pH: 6
  Total liquid volume: 50 ml Both batches were then extracted under alkaline conditions for 60 min (E stage).

E Stage
  2% pulp density
  Temperature: 60° C.
  Alkali: 80 g of NaOH/kg of pulp The degree of delignification was determined from the determination of the kappa values of both batches. The control value indicates the kappa value of the starting pulp after alkaline extraction. In order to investigate the effect of the combined treatment on the cellulose, the viscosity of the pulp samples was investigated. The viscosity determination was carried out according to the procedures as specified by TAPPI. The viscosity is indicated in ml/g.

TABLE 12

EXPERIMENTAL EVALUATION

Effect of the cellulase dose on delignification and viscosity of pulp (SW; K 16.6) when using a cellulase-containing sequence (CL) E

| Cellulase dose U/g of pulp | Kappa | Delignification (%) | Viscosity (ml/g) |
|---|---|---|---|
| 0 | 12.7 | 23.5 | 947 |
| 0.1 | 12.5 | 24.7 | 972 |
| 0.3 | 12 | 27.7 | 982 |
| 1 | 11.9 | 28.3 | 957 |
| 3 | 11.8 | 28.9 | 963 |
| 9 | 11.6 | 30.1 | 905 |
| 10 | 11.5 | 30.7 | 891 |
| 30 | 11.1 | 33.1 | 822 |
| 90 | 11 | 33.7 | 734 |

By increasing the cellulase dose, an improvement in the delignificability can be achieved up to a range of 9 U/g of pulp. On further increase of the dose, improvement is no longer achieved. The viscosity of the pulp remains almost constant up to a dosage of about 3 U/g. On increasing the dose further, a marked loss of viscosity occurs. With a suitable dosage (3 U/g in the example), the positive cellulase effect can be used to improve the delignification without damage already occurring to the fibers (viscosity decrease).

EXAMPLE 12

Effect of the pH on delignification by means of a laccase mediator system (LMS®) which contains cellulase as an additive.

In order to demonstrate the effect of pH, the delignification was compared in batches at different pHs. In a 500 ml laboratory autoclave, the batch described in the table below was incubated for 2 hours at 45° C. (water bath) with application of an oxygen partial pressure of 10 bar (CL stage).

(CL) Stage
  5 g of softwood pulp (abs. dry)
  Pulp density: 10%
  Laccase: 15 IU/g of pulp
  Cellulase from Trichoderma viride (Sigma): 2.5 U/g of pulp
  Mediator: N—OH-acetanilide: 10 mg/g of pulp
  pHs: 4, 5, 6, 7, 8
  Total liquid volume: 50 ml After the incubation, the batches were extracted under alkaline conditions for 60 min (E stage).

E Stage
  2% pulp density
  Temperature: 60° C.
  Alkali: 80 g of NaOH/kg of pulp The degree of delignification was determined from the determination of the kappa values of the pulps delignified in this system.

TABLE 13 pH dependence of delignification using a laccase mediator system which contains cellulase as an additive (pulp has kappa 16.6 after E stage)

| pH | Kappa | Delignification (rel %) |
|---|---|---|
| 4 | 12.9 | 22.3 |
| 5 | 12.5 | 24.7 |
| 6 | 11.1 | 33.1 |
| 7 | 14.7 | 11.4 |
| 8 | 16.3 | 1.8 |

Table 13 shows that the laccase mediator system which contains cellulase as an additive shows a distinct pH profile with an optimum for the selected components in the range of pH 6 in the delignification.

EXAMPLE 13

Effect of the mediator on delignification by means of a laccase mediator system (LMS®) which contains cellulase as an additive.

In a 500 ml laboratory autoclave, the reference batches described in the table below were incubated for 2 hours at 45° C. (water bath) with application of an oxygen partial pressure of 10 bar (L stage).
L Stage (comparison experiment)
  5 g of softwood pulp (abs. dry)
  Pulp density: 10%
  Laccase: 15 IU/g of pulp
  Mediator: N—OH-acetanilide: 10 mg/g of pulp
  pH: pH 6.0
  Total liquid volume: 50 ml In order to determine the positive effect of an enzymatic additive such as, for example, cellulase, cellulase from *Trichoderma viride* (Sigma) was added to a batch corresponding to the L stage as a further additive (CL stage), such that the batch had the following composition:
(CL) Stage
  5 g of softwood pulp (abs. dry)
  Pulp density: 10%
  Laccase: 15 IU/g of pulp
  Cellulase: 2.5 U/g of pulp
  Mediator: N—OH-acetanilide: 10 mg/g of pulp
  pH: 6.0
  Total liquid volume: 50 ml Both batches were then extracted under alkaline conditions for 60 min (E stage).
E Stage
  2% pulp density
  Temperature: 60° C.
  Alkali: 80 g of NaOH/kg of pulp The degree of delignification was determined from the determination of the kappa values. The starting pulp had a kappa value of 16.6 after alkaline extraction.

TABLE 14

Delignification (rel %) using the laccase mediator system which contains cellulase as an additive in comparison with a cellulase-free system

| | NHA | HBT | Vio | HPI |
|---|---|---|---|---|
| Without cellulase LE | 23.3 | 9.1 | 15.2 | 6.1 |
| With cellulase (CL) E | 33.1 | 13.3 | 21.1 | 14.5 |

The addition of cellulase increases the delignification of a softwood pulp compared with a cellulase-free reference in the presence of all mediators used.

EXAMPLE 14

Delignification of various pulps using a laccase mediator system (LMS®) which contains cellulase and xylanase as additives In a 500 ml laboratory autoclave, the reference batches described in the table below were incubated for 2 hours at 45° C. (water bath) with application of an oxygen partial pressure of 10 bar (L stage).
L Stage (comparison experiment)
  5 g of various pulps (abs. dry)
  Pulp density: 10%
  Laccase: 15 IU/g of pulp
  Mediator: N—OH-acetanilide: 10 mg/g of pulp
  pH: 6.0
  Total liquid volume: 50 ml In order to determine the positive effect of several simultaneous enzymatic additives, such as, for example, cellulase and xylanase, cellulase from *Trichoderma viride* (Sigma) and xylanase were added to batches corresponding to the L stage as further additives (LXC stage), such that the batches had the following composition:
(LXC) Stage
  5 g of various pulps (abs. dry)
  Pulp density: 10%
  Laccase: 15 IU/g of pulp
  Cellulase: 0.1 U/g of pulp
  Xylanase: 2.0 U/g
  Mediator: N—OH-acetanilide: 10 mg/g of pulp
  pH: 6.0
  Total liquid volume: 50 ml All batches were extracted under alkaline conditions for 60 min after incubation (E stage).
E Stage
  2% pulp density
  Temperature: 60° C.
  Alkali: 80 g of NaOH/kg of pulp The degree of delignification was determined from the determination of the kappa values. The degrees of delignification achievable (rel. %) of a treatment with laccase/mediator (LE) (comparison experiment) were compared with the treatment with laccase/mediator/ cellulase/xylanase (LXC)E.

TABLE 15

Comparison of delignifications of a laccase mediator system provided with a cellulase and xylanase addition - sequence (LXC)E - using the additive-free system - sequence LE - .
Various pulps were tested.

| Pulp type* | Kappa LE | Kappa (LXC)E | Delignif. LE | Delignif. (LXC)E | Delign. increase (%) |
|---|---|---|---|---|---|
| SwKPu | 17.4 | 15.9 | 15.5 | 22.8 | 7.3 |
| SwKPuO | 10.5 | 9.3 | 30 | 38.3 | 8.3 |
| SwKPuO | 10.2 | 9.1 | 23.3 | 31.6 | 8.3 |
| SwKPuO | 6.2 | 5.1 | 31.9 | 44 | 12.1 |
| SwKPuO | 12.7 | 11.5 | 23.5 | 30.7 | 7.2 |
| SwKPuO | 9 | 8.1 | 28 | 35.2 | 7.2 |
| SwKPuO | 10.9 | 10.2 | 33.5 | 37.8 | 4.3 |
| SwKPu-2O | 7.1 | 6.1 | 23.7 | 33.9 | 10.2 |
| HwKPu | 10.5 | 8.9 | 12.5 | 25.8 | 13.3 |
| HwKPuO | 7.6 | 7.1 | 29.6 | 34.3 | 4.7 |

*SW softwood
HW hardwood
K kraft
O Oxygen treated
Pu Pulp

In the case of all pulps, a marked increase in delignification can be achieved by means of a laccase mediator system by the simultaneous addition of cellulase and xylanase.

While a few embodiments of the present invention have been shown and described, it is to be understood that many changes and modifications may be made thereunto without departing from the spirit and scope of the invention as defined in the appended claims.

What is claimed is:

1. A process for the delignification of lignin-containing material comprising the steps of
   providing an aqueous suspension of lignin-containing material,
   adding to the suspension an oxidoreductase, comprising laccase, at least one oxidant for the oxidoreductase, at least one mediator and at least one enzymatically active additive comprising xylanase;
   mixing said xylanase simultaneously with the aqueous suspension of the lignin-containing material; and
   preventing the mediator from inactivating the oxidoreductase and the enzyme additive xylanase; and
   wherein the mediator is selected from the group consisting of violuric acid (Vio), N—OH-acetanilide (NHA), —OH-phthalimide (HPI), disodium 1-nitroso-2-naphthol-3,6-disulfonate hydrate (1-NNS), and 2-nitroso-1-naphthol-4-sulfonic acid tetrahydrate (2-NNS).

2. The process as claimed in claim 1, wherein 0.1–100 IU of oxidoreductase are employed per g of lignin-containing material (dry weight).

3. The process as claimed in claim 1,
   wherein the aqueous suspension contains pulp and the mediator is employed in amounts of 1–500 mmol/kg of pulp.

4. The process of claim 1, comprising laccase and a mixture of xylanase and cellulase.

5. A process for the delignification of lignin-containing material comprising the steps of
   providing an aqueous suspension of lignin-containing material;
   adding to the suspension an oxidoreductase comprising laccase, at least one oxidant for the oxidoreductase, at least one mediator, and at least one enzymatically active additive comprising xylanase;
   mixing said xylanase additive in any desired sequence with the aqueous suspension of the lignin-containing material;
   preventing the mediator from inactivating the oxidoreductase and the enzyme additive xylanase; and
   wherein the mediator is selected from the group consisting of violuric acid (Vio), N—OH-acetanilide (NHA), —OH-phthalimide (HPI), disodium 1-nitroso-2-naphthol-3,6-disulfonate hydrate (1-NNS), and 2-nitroso-1-naphthol-4-sulfonic acid tetrahydrate (2-NNS).

6. The process as claimed in claim 5, wherein 0.1–100 IU of oxidoreductase are employed per g of lignin-containing material (dry weight).

7. The process as claimed in claim 5,
   wherein aqueous suspension contains pulp and the mediator is employed in an amount of 1–500 mmol/kg of pulp.

8. The process of claim 5, comprising laccase and a mixture of xylanase and cellulase.

9. A multicomponent composition for modifying, degrading or bleaching a substance selected from the group consisting of lignin and lignin-containing materials comprising
   an oxidoreductase comprising laccase and an oxidant for the oxidoreductase;
   at least one enzymatically active additive comprising xylanase and a mediator which does not inactivate the laccase oxidoreductase and the enzymatically active additive;
   wherein the mediator is selected from the group consisting of violuric acid (Vio), N—OH-acetanilide (NHA), —OH-phthalimide (HPI), disodium 1-nitroso-2-naphthol-3,6-disulfonate hydrate (1-NNS), and 2-nitroso-1-naphthol-4-sulfonic acid tetrahydrate (2-NNS).

10. The multicomponent composition of claim 9, comprising laccase and a mixture of xylanase and cellulase.

* * * * *